United States Patent
Summerton et al.

(10) Patent No.: US 7,074,332 B2
(45) Date of Patent: Jul. 11, 2006

(54) MULTISTAGE HEMODIAFILTRATION/HEMOFILTRATION METHOD AND APPARATUS

(75) Inventors: James Summerton, Hillsdale, NJ (US); Gregory R. Collins, Monroe, NY (US); Edward Spence, Bronx, NY (US)

(73) Assignee: Nephros, Inc., New York, NY (US)

( * ) Notice: Subject to any disclaimer, the term of this patent is extended or adjusted under 35 U.S.C. 154(b) by 283 days.

(21) Appl. No.: 10/451,204

(22) PCT Filed: Dec. 20, 2001

(86) PCT No.: PCT/US01/50503

§ 371 (c)(1), (2), (4) Date: Jun. 18, 2003

(87) PCT Pub. No.: WO02/49745

PCT Pub. Date: Jun. 27, 2002

(65) Prior Publication Data

US 2004/0068219 A1    Apr. 8, 2004

Related U.S. Application Data

(60) Provisional application No. 60/257,191, filed on Dec. 20, 2000.

(51) Int. Cl.
*B01D 61/24* (2006.01)
*B01D 61/28* (2006.01)
*B01D 61/32* (2006.01)
*B01D 63/00* (2006.01)
*B01D 61/00* (2006.01)

(52) U.S. Cl. .................. 210/646; 210/321.72; 210/645; 210/739; 210/650; 210/321.71; 210/929; 210/647; 210/323.2; 210/416.1; 210/434; 210/87; 210/90; 210/97

(58) Field of Classification Search ............... None
See application file for complete search history.

(56) References Cited

U.S. PATENT DOCUMENTS

| | | | |
|---|---|---|---|
| 5,660,722 A | 8/1997 | Nederlof | |
| 5,846,419 A | 12/1998 | Nederlof | |
| 5,882,516 A | 3/1999 | Gross et al. | |
| 6,303,036 B1 * | 10/2001 | Collins et al. | 210/646 |
| 6,406,631 B1 * | 6/2002 | Collins et al. | 210/646 |
| 6,423,231 B1 * | 7/2002 | Collins et al. | 210/646 |

FOREIGN PATENT DOCUMENTS

| WO | WO 200006292 A1 * | 2/2000 |
|---|---|---|
| WO | WO 200025902 A1 * | 5/2000 |

* cited by examiner

*Primary Examiner*—John Kim
*Assistant Examiner*—Krishnan S. Menon
(74) *Attorney, Agent, or Firm*—Darby & Darby

(57) ABSTRACT

In a blood dialysis system including a source of substitution fluid (10) and a blood dialysis machine, a hemodiafiltration system having a first dialyzer (1) including a first blood compartment (4) having a first blood inlet which receives blood to be cleaned and a first blood outlet which discharges partially diafiltered blood and a first dialysate compartment (5) having a first dialysate inlet and a first dialysate outlet, means (8) for mixing the partially diafiltered blood with substitution fluid from the source to obtain a blood/substitution fluid mixture, and a second hemofilter (2) including a second blood compartment (11) having a second blood inlet which receives the blood/substitution fluid mixture and a second blood outlet which discharges filtered blood and a second permeate compartment (12) having a second permeate outlet.

20 Claims, 14 Drawing Sheets

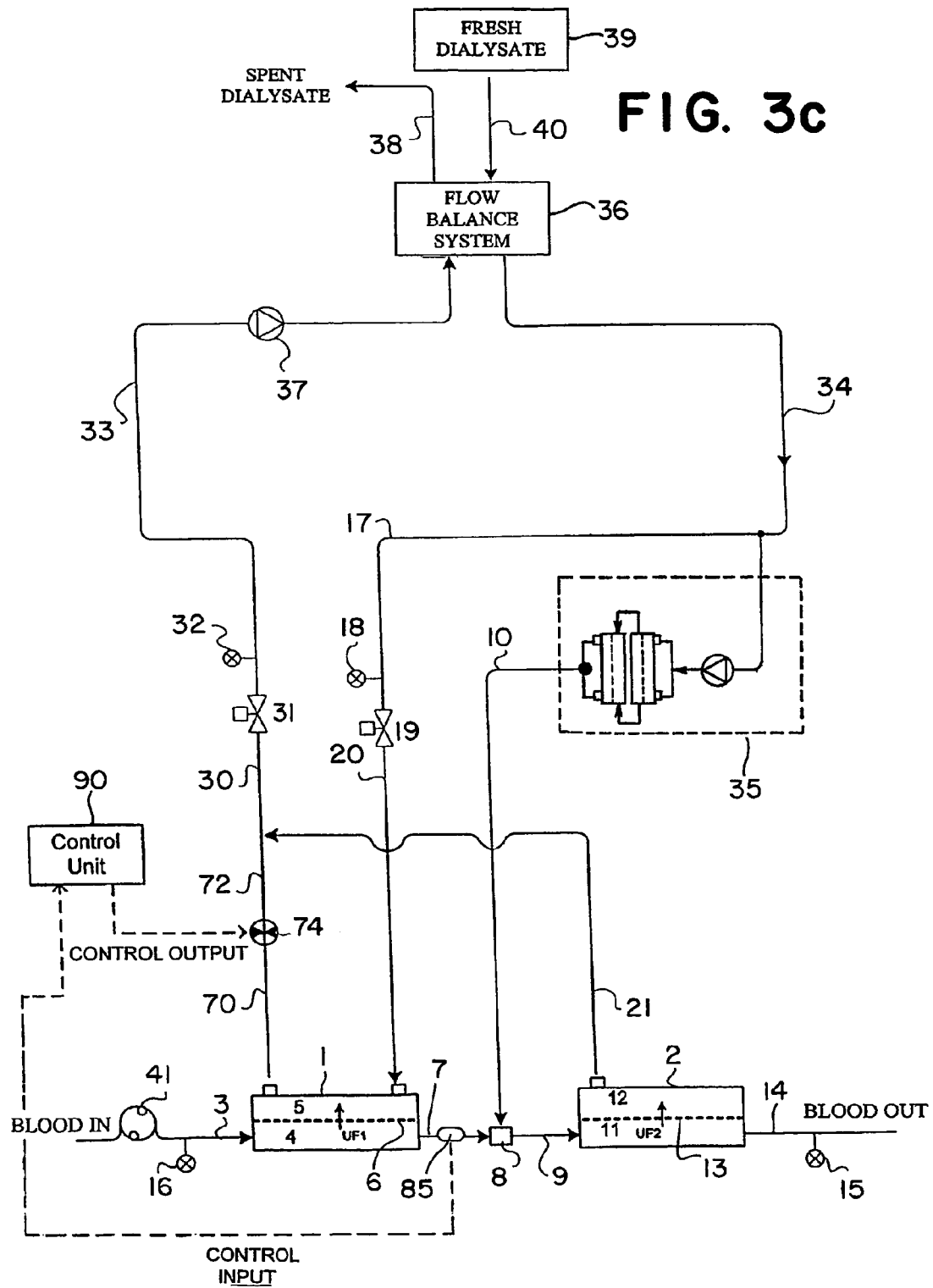

MULTISTAGE HEMODIAFILTRATION/HEMOFILTRATION METHOD AND APPARATUS

CROSS REFERENCE TO RELATED APPLICATION

This is a U.S. national phase application under 35 U.S.C. §371 of International patent application serial No. PCT/US01/50503, filed Dec. 20, 2001 and claims the benefit of U.S. provisional application Ser. No. 60/257,191, filed Dec. 20, 2000, which is hereby incorporated by reference in its entirety. The International Application was published in English on Jun. 27, 2002 as WO 02/049745 A1 under PCT Article 21(2).

TECHNICAL FIELD

The invention relates to blood cleansing systems in general and, more particularly, to a blood cleansing modality including a hemodiafiltration stage as well as a hemofiltration stage.

BACKGROUND OF THE INVENTION

Hemodiafiltration combines both standard hemodialysis and hemofiltration into one process, whereby a dialyzer cartridge containing a high flux membrane is used to remove substances from the blood both by diffusion and by convection. The removal of substances by diffusion is accomplished by establishing a concentration gradient across a semipermeable membrane by flowing a dialysate solution on one side of the membrane while simultaneously flowing blood on the opposite side of the membrane. In existing systems, to enhance removal of substances using hemodiafiltration, a solution called substitution fluid is continuously added to the blood either prior to the dialyzer cartridge (pre-dilution) or after the dialyzer cartridge (post-dilution). An amount of fluid equal to that of the added substitution fluid is ultrafiltered across the dialyzer cartridge membrane carrying with it additional solutes.

Substitution fluid is usually purchased as a sterile/non-pyrogenic fluid contained in large flexible bags or is produced on-line by filtration of a non-sterile dialysate through a suitable filter cartridge rendering it sterile and non-pyrogenic. Techniques for online production of substitution fluid have been described in the literature, for example, in D. Limido et al., "*Clinical Evaluation of AK-100 ULTRA for Predilution HF with On-Line Prepared Bicarbonate Substitution Fluid. Comparison with HD and Acetate Postdilution HF*", *International Journal of Artificial Organs*, Vol. 20, No. 3 (1997), pp. 153–157.

In general, existing hemodiafiltration schemes use a single dialyzer cartridge containing a high flux semi-permeable membrane, for example see P. Ahrenholz et al., "*On-Line Hemodiafiltration with Pre- and Postdilution: A Comparison of Efficiency*", *International Journal of Artificial Organs*, Vol. 20, No. 2 (1997), pp. 81–90. In prior art systems, substitution fluid is introduced into the blood stream either in a pre-dilution mode or in a post-dilution mode relative to the dialyzer cartridge. The preferred mode for maximal removal of both small and large substances from blood, in accordance with the prior art, is the post-dilutional mode because this mode achieves the highest concentration gradient between the blood and the dialysate fluid. In a typical pre-dilution mode with on-line generation of substitution fluid, however, the bloodside concentration is lowered relative to the dialysate fluid. As a result, removal (or clearance) of substances can decrease, as described in The International Journal of Artificial Organs, 1997, vol. 20, pp. 81–90. This decrease is particularly apparent for smaller molecules, like urea, where mass transport is driven more by diffusion than by convection. Use of two dialyzer cartridges in a hemodiafiltration scheme has been reported in J. H. Miller et al., "*Technical Aspects of High-Flux Hemodiafiltration for Adequate Short (Under 2 Hours) Treatment*", *Transactions of the American Society Artificial Internal Organs* (1984), pp. 377–380. In this scheme, the substitution fluid is reverse-filtered through the membrane of the second dialyzer cartridge simultaneously with the filtration of fluid across the membrane of the first dialyzer cartridge. A variation of this method is described in B. Nederlof, "HEMO (DIA)FILTRATION APPARATUS AND FILTRATE FLOW REGULATOR", U.S. Pat. No. 5,600,722 (1997), wherein a dialysate pump between the dialyzers is used to regulate the amount of reverse-filtration in the second dialyzer cartridge. Another two cartridge system is described in P. Ghezzi et al., "BLOOD PURIFYING EQUIPMENT PARTICULARLY FOR THE TREATMENT OF PATIENTS SUFFERING FROM RENAL INSUFFICIENCY, AND A METHOD OF PRODUCING A REINFUSION LIQUID FOR Hemodiafiltration (HDF)", U.S. Pat. No. 5,194,157 (1993). In this patent, blood flows through a first filter cartridge whereby plasma water is filtered across a semi-permeable membrane as a means to remove blood substances by convection. A process, such as adsorption, is then performed on a portion of the filtered plasma water to produce an infusion fluid that is reintroduced back into the blood stream. The filtered blood then passes through a dialyzer cartridge containing a semi-permeable membrane whereby removal of blood substances occurs by diffusion into a dialysate fluid stream. Thus, blood is subjected to a hemofiltration process in a first cartridge stage followed by a hemodialysis process in a second cartridge stage.

Certain trade-offs exist with respect to removal of different size molecules when comparing pre-dilution hemodiafiltration and post-dilution hemodiafiltration using a single dialyzer cartridge. For example, on-line pre-dilution hemodiafiltration schemes generally achieve higher convection filtration rates, compared to on-line post-dilution hemodiafiltration, enhancing removal of large molecules; however, the increased removal by convection comes at the expense of reducing the removal of small molecules, such as urea and creatinine. In on-line post-dilution hemodiafiltration schemes, on the other hand, the amount of fluid that may be filtered from the blood as it passes through the dialyzer cartridge is limited. Specifically, the filterable amount is dependent upon several factors, which include blood flow rate, blood hematocrit, and blood protein concentration. Typically, the filterable amount is 20% to 30% of the incoming blood flow rate. For example, at a blood flow rate of 300 milliliter per minute (ml/min), the filterable amount is typically limited to 90 ml/min. In the two dialyzer approach described by J. H. Miller et al., the filterable amount is also limited to about 20% to 30% of the blood flow because forward filtration occurs only in the first dialyzer. The second dialyzer then re-infuses the fluid lost in the first dialyzer by reverse-filtration, as in on-line post-dilution hemodiafiltration. In the approach described by P. Ghezzi et al., the filterable amount is also limited to about 20% to 30% of the blood flow because forward filtration occurs only in the first hemofilter cartridge.

SUMMARY OF THE INVENTION

It is an object to provide a hemodiafiltration/hemofiltration method and apparatus that overcome the convection limitation associated with on-line post-dilution hemodiafiltration schemes using a single dialyzer cartridge, as well as the loss of small molecule clearance associated with on-line pre-dilution hemodiafiltration schemes using a single dialyzer cartridge.

It is another object to provide an improved method of hemodiafiltration/hemofiltration using a combination of two dialyzers, a dialyzer and hemofilter, or a single cartridge having a dialyzer stage and a hemofilter stage. In addition, methods and systems are provided for regulating the amount of ultrafiltration in each of the two dialyzer/hemofilter stages. It will be understood by persons of ordinary skill in the art that, although various embodiments are described herein in the context of hemodiafiltration/hemofiltration using substitution fluid which is produced "on-line", the present hemodiafiltration methods and systems can be readily modified to be used in conjunction with other sources of substitution fluid.

According to one exemplary embodiment, a hemodiafiltration/hemofiltration system is provided and includes at least two dialyzer cartridges, a dialyzer cartridge and hemofilter cartridge, or a single cartridge with a dialyzer stage and a hemofiltration stage, which perform hemodiafiltration in one stage and hemofiltration in a second stage, and at least one sterility filter which converts dialysate fluid into a sterile substitution fluid, preferably on-line. Additional components (e.g. pumps, throttling valves, mixing chambers, control units) may also be used in conjunction with the invention, as described below.

Each dialyzer contains a semi-permeable membrane that is embedded within a jacket or housing. The semi-permeable membrane separates the device into a blood compartment and a dialysate compartment. The hemofilter also contains a semi-permeable membrane that is embedded within a jacket or housing. The semi-permeable membrane separates the device into a blood compartment and permeate compartment. At least one dialyzer cartridge and one hemofilter cartridge is used to carry out the hemodiafiltration process in accordance with the invention. It should be understood by those skilled in the art, that a dialyzer containing a high flux membrane can be used as a hemofilter cartridge whereby one of the dialysate ports is capped off. Alternatively, the dialyzer and hemofilter cartridges may be combined into a single cartridge including a dialyzer section and a hemofilter section. The at least one sterility filter cartridge preferably also contains a semi-permeable membrane. This filter is used to remove bacteria, endotoxins, and other particulate from dialysate in order to generate a suitable substitution fluid stream, preferably on-line.

During operation of the system, blood enters the bloodside compartment of the first dialyzer cartridge, wherein a portion of plasma water is filtered across the semi-permeable membrane into the adjacent dialysate compartment. Upon exiting the first dialyzer cartridge, substitution fluid is added back to the blood at a rate higher than the rate at which fluid is filtered out of the blood in the first dialyzer cartridge. The diluted blood then enters the bloodside compartment of the second hemofilter cartridge, wherein additional plasma water is filtered across the semi-permeable membrane into the adjacent permeate compartment at a rate substantially equal to the difference between the rate at which substitution fluid is added to the blood upon exiting the first dialyzer cartridge and the filtration rate at the first dialyzer cartridge.

Thus, the substitution fluid acts as a post-dilution fluid relative to the first dialyzer cartridge as well as a pre-dilution fluid relative to the second hemofilter cartridge. The advantage of operating the system in this mode is the improved clearance of larger molecular weight substances because the total filtration of plasma water can be effectively increased (e.g., 40% to 100% of the incoming blood flow rate) compared to that of a single dialyzer cartridge operating in a post-dilution mode or two dialyzers in series with the second dialyzer being operated in a reverse-filtration mode.

Dialysate fluid for the system of the invention may be generated using existing methods. The dialysate fluid enters the first dialyzer cartridge and flows counter-current with respect to the blood flow direction. The dialysate fluid acts to set-up a concentration gradient against the bloodside fluid, thereby inducing diffusion of solutes across the semi-permeable membrane. As the dialysate traverses through the dialysate compartment, the dialysate flow rate increases due to plasma water being filtered across into the dialysate compartment as described above. Upon exiting the first dialyzer, the spent dialysate fluid combines with filtrated plasma water from the second hemofilter cartridge. The combined fluid stream is transported back to the dialysis machine. By including additional components, for example, a flow regulating pump or a fluid restricting device (e.g. throttling valve), located at the spent dialysate stream exiting the first dialyzer cartridge, it is possible to regulate the amount of plasma water filtered across the membranes of the respective cartridges. This improved control enables the system to achieve even higher effective substitution rates.

Preparation of the sterile/non-pyrogenic substitution fluid may be accomplished by drawing a portion of fresh dialysate solution from a fresh dialysate inlet line and passing it through at least one sterile filter cartridge prior to introducing it into the blood between the two dialyzer stages. In the present scheme, the dialysis machine generally performs all of its normal functions, such as preparing dialysate, metering dialysate flow rate, balancing flow, monitoring pressures, ultrafiltration control, monitoring spent dialysate for presence of blood etc.

The present invention may be implemented in a number of ways. In one embodiment, substitution fluid is added to the blood between the dialyzer and hemofilter stages without additional components to regulate the filtration in each stage. In a second embodiment, a flow restrictor is used at the spent dialysate stream as a means to raise the transmembrane pressure (TMP) across the hemofilter cartridge relative to the TMP across the dialyzer cartridge. In the third, fourth, and fifth embodiment, a feedback control loop is used as means to adjust the aperture setting of a throttling valve also located at the spent dialysate stream. In the third embodiment, control is based on pressure inputs as a means to control the relative transmembrane pressures of the two stages. The fourth and fifth embodiments use a flow meter and a hematocrit sensor as control inputs to adjust the aperture setting of the throttling valve. In a sixth and seventh embodiment, a flow regulating pump is added at the spent dialysate stream as a means for controlling the relative filtration rates of the dialyzer/hemofilter stages. The sixth embodiment is based on either a pressure feedback control loop to regulate the relative TMP's of the two stages or a feedforward control loop based on blood, dialysate, and substitution flow rates. The seventh embodiment includes a check valve in parallel with the flow regulating pump as a means to make the control loop independent of the substitution flow rate. In an eighth embodiment, a permeate pump is used at the permeate stream from the hemofilter cartridge.

Feedback control loops based on pressures or flow rates are used as a means for controlling the relative TMP's or filtration rates of the dialyzer/hemofilter stages, respectively. In a ninth, tenth, and eleventh embodiment, an inter-stage blood pump is used to regulate blood flow between the dialyzer and hemofilter stages. The ninth embodiment uses a feedback control loop based on either pressures or flow rates similar to the eighth embodiment as a means to control the inter-stage blood pump. The tenth embodiment uses a hematocrit sensor at the blood exiting the first dialyzer cartridge as a control input to the inter-stage blood pump. The eleventh embodiment uses a check valve in parallel with the inter-stage blood pump similar to the seventh embodiment.

BRIEF DESCRIPTION OF THE DRAWINGS

FIG. 3c is a schematic illustration of a two stage hemodiafiltration system in accordance with one embodiment, using a throttling valve controlled by a feedback loop including an inter-stage blood hematocrit measurement control input;

DETAILED DESCRIPTION OF THE INVENTION

Figure 1A:
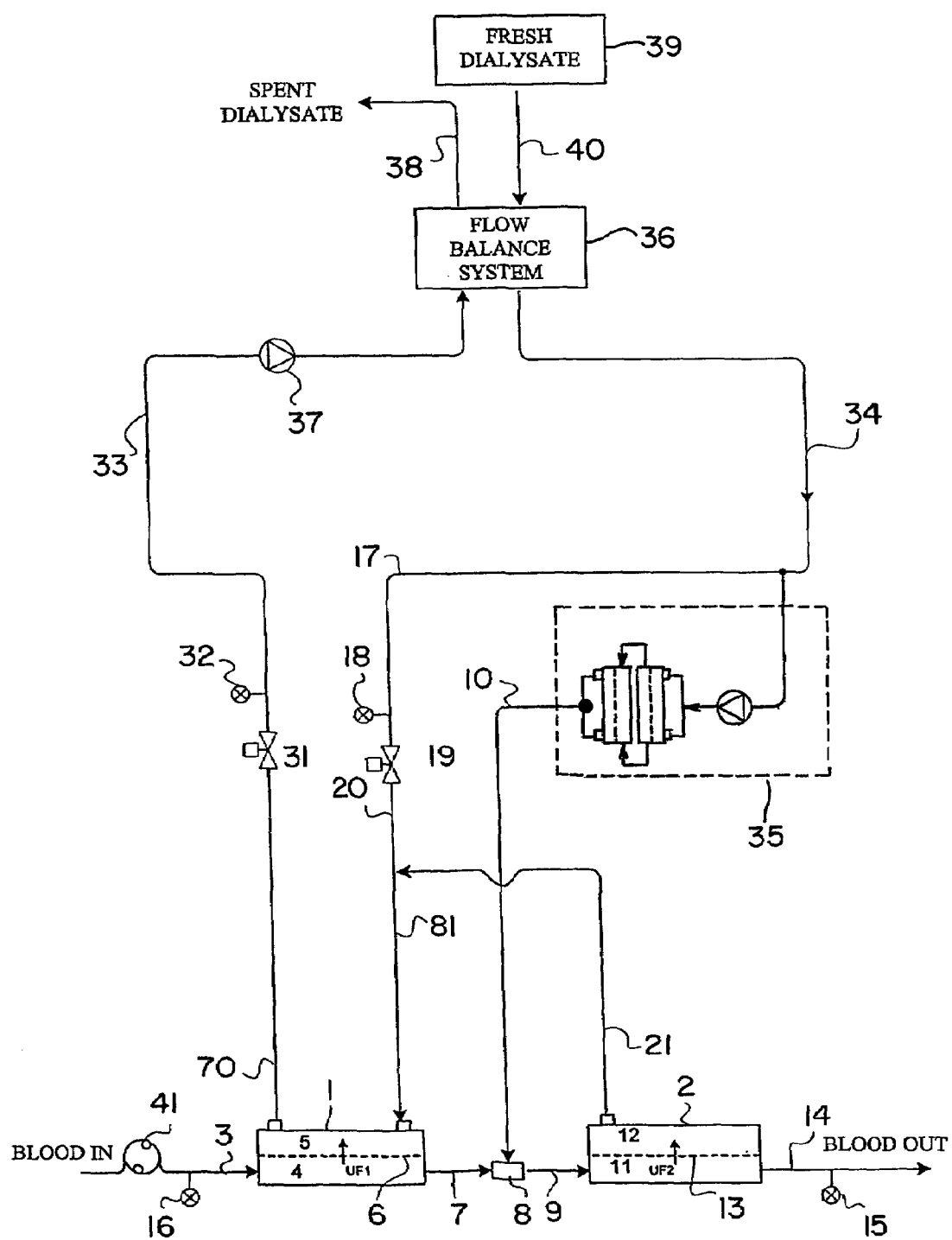
FIG. 1a is a schematic illustration of a two stage hemodiafiltration system in accordance with one embodiment.

In the embodiment of FIG. 1a, blood to be cleaned 3 is pumped by a blood pump 41 and enters a first dialyzer cartridge 1. As shown in FIG. 1a, inlet blood circuit pressure 16 (denoted "Pa") is measured upon exiting blood pump 41, to be used as a monitoring and control parameter of the blood flow prior to entering the first dialyzer cartridge 1. The blood carrying tubing may be any suitable bloodline tubing known in the art, for example a flexible polyvinylchloride (PVC) tubing. The blood flow rate is generally in the range of about 200 to about 700 ml/min, preferably about 300 to about 600 ml/min.

Dialyzer cartridge 1 contains a semi-permeable membrane 6 that divides the dialyzer into a blood compartment 4 and a dialysate compartment 5. As blood passes through the blood compartment, plasma water containing blood substances is filtered across the semi-permeable membrane 6 (denoted "UF1" in FIG. 1a). Additional blood substances are transferred across the semi-permeable membrane 6 by diffusion which is induced by a difference in concentration between the blood compartment 4 and the dialysate compartment 5. The dialyzer cartridge 1 used may be of any type suitable for hemodialysis, hemodiafiltration, hemofiltration, or hemoconcentration, as are known in the art. Preferably, the dialyzer 1 contains a medium or high flux membrane. Examples of suitable cartridges 1 include but are not limited to the Fresenius F60, F80 available from Fresenius Medical Care of Lexington, Mass.; Baxter CT 110, CT 190, Syntra 160 available from Baxter of Deerfield, Ill.; Hospal Filtral 16 available from Hospal of Switzerland; Polyflux 14S, 21S, 24S available from Gambro of Lund, Sweden; Minntech Hemocor HPH 1000, Primus 1350, 2000 available from Minntech of Minneapolis, Minn.

Partially diafiltered blood 7 exits dialyzer cartridge 1 and mixes with sterile substitution fluid 10 in a mixing chamber 8. As used herein, the term "partially diafiltered blood" refers to blood that has undergone a hemodiafiltration process and as a result, an amount of toxins have been removed from the blood. The blood/substitution fluid mixture 9 then enters a hemofilter cartridge 2. The hemofilter cartridge 2 contains a semi-permeable membrane 13 that divides the cartridge 2 into a blood compartment 11 and a permeate compartment 12. As blood passes through blood compartment 11, plasma water containing blood substances are filtered across the semi-permeable membrane 13 (denoted as UF2). The hemofilter cartridge 2 can be of any type used for hemodialysis, hemodiafiltration, hemofiltration, or hemoconcentration. Preferably the hemofilter cartridge 2 contains a medium or high flux membrane. The hemofiltration process removes a further amount of toxins from the partially diafiltered blood received from the dialyzer cartridge 1. Examples of the suitable cartridges include but are not limited to the Fresenius F60, Baxter CT 110, Hospal Filtral 16, or Minntech Hemocor HPH 400. The cleansed blood 14 is returned to the patient (not shown) through bloodline PVC tubing, as is known in the art. Pressure of the exiting blood may also be monitored through a pressure sensor 15.

Fresh dialysate solution 39 may be prepared using any method known in the art, for example the volumetric proportioning method used in the Fresenius 2008 dialysis machine, available from Fresenius Medical Care, Lexington, Mass. Dialysate fluid is conveyed to a flow balancing system 36 via fluid path 40. The flow balancing system 36 may include any suitable devices known in the art, for example, volumetric balance chambers as used in the Fresenius 2008 dialysis machine, or dual flow meters as used in the Baxter 1550 dialysis machine, available from Baxter, Deerfield, Ill., USA. Fresh dialysate from the flow balance system 36 flows through a conduit 34. A portion of the fresh dialysate fluid may be used as raw substitution fluid for an on-line substitution fluid delivery system 35, which may include any suitable substitution fluid delivery system known in the art. The remaining dialysate fluid 17, not used for producing substitution fluid, is used as dialysate fluid which enters the dialysate inlet port of the first dialyzer cartridge 1. The pressure of the inlet dialysate fluid may be measured by a pressure sensor 18 (the pressure denoted "Pdi"). The fresh dialysate fluid 20 may combine with plasma water 21 that is filtered across the semi-permeable membrane 13 of the hemofilter cartridge 2. The dialysate and plasma water mixture 81 enters the dialysate compartment 5 and flows counter current with respect to the blood flow in the adjacent compartment 4. During hemodiafiltration, plasma water filters across the semi-permeable membrane 6 and mixes with the dialysate fluid. A mixture of the dialysate fluid and the filtered plasma water exits the dialyzer cartridge 1 and flows through a conduit 70 that leads back to the flow balance system 36. Pressure of this fluid may be measured by a pressure sensor 32 (measuring pressure "Pdo").

Figure 1B:
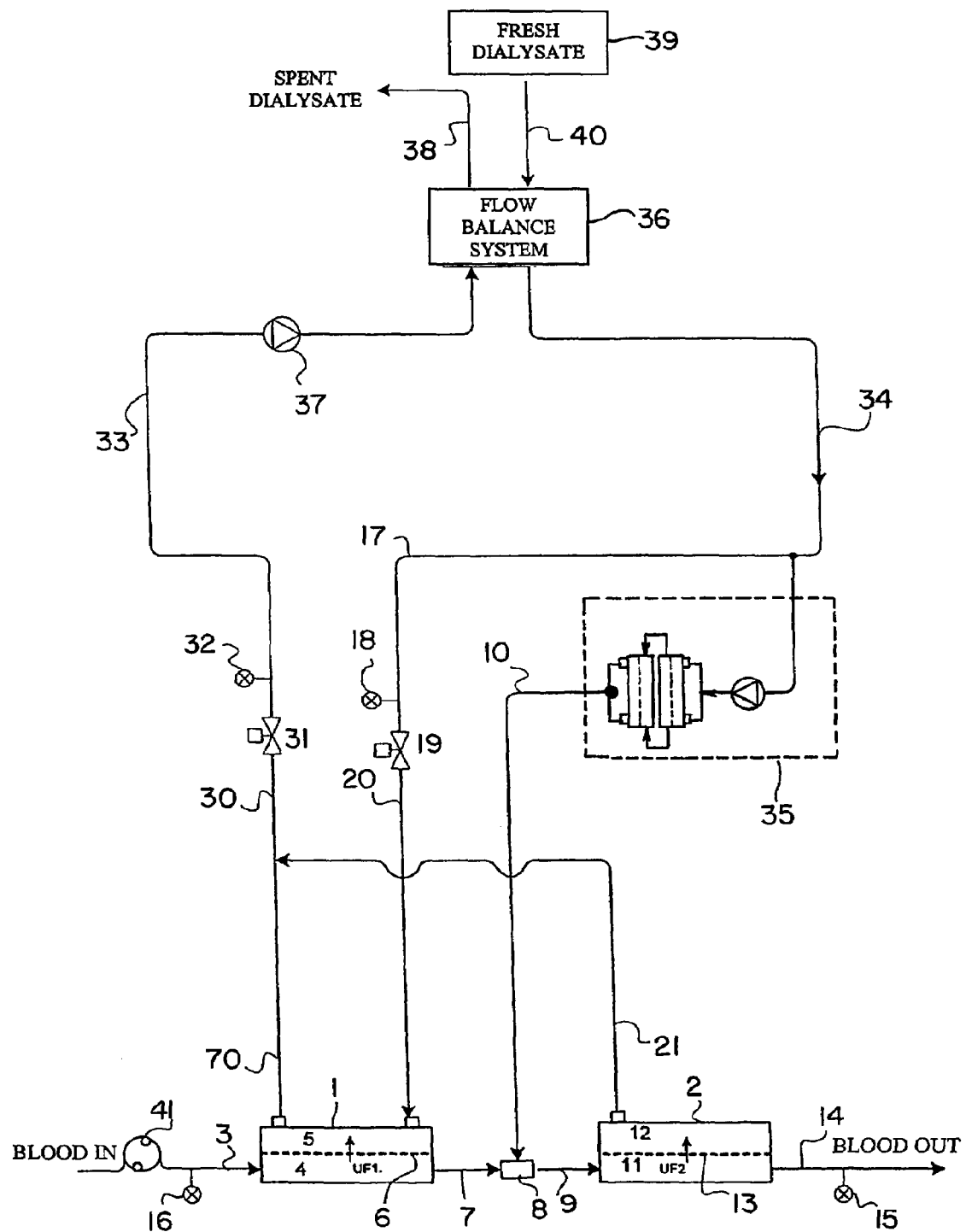
FIG. 1b is a schematic illustration of a two stage hemodiafiltration system in accordance with one embodiment with plasma water from second hemofilter stage bypassing the first dialyzer stage.

FIG. 1b shows a second embodiment. In this second embodiment, the plasma water that has been filtered across the semi-permeable membrane 13 of the hemofilter cartridge 2 does not combine with the fresh dialysate stream that is introduced to the dialysate inlet port of the first dialyzer cartridge 1. Instead, the plasma water 21 bypasses the first dialyzer cartridge 1 and combines with the spent dialysate fluid 70 that exits the first dialyzer cartridge 1. This spent dialysate/plasma water mixture 30 leads back to the flow balance system 36. The advantage of this is that the fresh dialysate stream 20 is not exposed to any potential plasma proteins that may be present in the plasma water 21. Thus risk of cross contamination between patients is substantially reduced.

It will be apparent to those skilled in the art that the hemodiafiltration method and system of the present invention is significantly more efficient than current methods and systems using a single dialyzer, in both pre- and post-dilution modes of operation, as well as methods using two dialyzers, performing forward filtration and reverse-filtration, respectively. An advantage of the system of the present invention is the ability to achieve higher substitution rates than the rates achieved by prior art systems and methods. The present invention overcomes the limitation of the prior art systems, in which not more than about 30% of the incoming blood flow may be filtered by a single cartridge before adding substitution fluid. In prior art systems, it is not possible to remove or filter more than about 30% of the incoming blood flow rate without causing the blood to become hemoconcentrated and overly viscous. In the embodiment described above, by adding the substitution fluid to the blood prior to entering the blood compartment 11 of the second hemofilter 2, additional fluid (plasma water) is filtered across the second semi-permeable membrane 13, thus enhancing the overall plasma water filtered from the blood side to the dialysate side of both cartridges 1, 2. The higher substitution rate has the distinct advantage of removing larger molecular weight toxins by convection. In prior art systems operating in a pre-dilution hemodiafiltration mode, the removal of small molecular weight toxins is reduced significantly. This is because the concentration gradient between the blood and the dialysate is reduced whenever fluid is added to the blood prior to flowing through the dialyzer cartridge. Since a scheme similar to a pre-dilution scheme only occurs relative to the second hemofilter 2 in the embodiment described above, the pre-dilution effect is minimized because most of the small molecular weight toxins were removed in the first dialyzer stage which is operated in a post dilution mode. The net effect is an improvement in clearance of small molecular weight toxins compared to pre-dilution hemodiafiltration and an improvement in clearance of large molecular weight toxins when compared to post dilution hemodiafiltration methods using either a single dialyzer or two dialyzers with back filtration occurring in the second dialyzer. A fundamental difference between the two stage hemodiafiltration method described herein and current methods using two dialyzers is that forward filtration of plasma water occurs in both stages simultaneously with counter-current flow of dialysate through the first dialyzer stage, as opposed to prior art systems which perform forward filtration of plasma water in one dialyzer and reverse-filtration of dialysate in a second dialyzer, with a counter-current flow of dialysate through both dialyzer stages. Additionally, substitution fluid is added directly to the blood stream between the two dialyzer stages, in contrast to the reverse filtering of the substitution fluid through one of the dialyzer membranes in accordance with the prior art.

It has been discovered that the second embodiment may be further improved by incorporating a control scheme to regulate the amount of filtration in each of the two dialyzer stages 1, 2. Such control helps avoid the inherent pressure drop which results from operating cartridges in a series configuration. It has been observed that, without filtration control, the transmembrane pressure (TMP) in the first dialyzer is inherently higher than the TMP in the second hemofilter. Since each dialyzer and hemofilter has a maximum allowable TMP, theoretically, it is possible that the system would operate at a substitute fluid rate exceeding the TMP limit. Further, since the TMP of the second hemofilter is inherently lower than that of the first dialyzer, in essence, the filtering capacity of the second hemofilter may be underutilized. Therefore, by incorporating additional fluid path components, the present invention enables higher, preferably maximal, utilization of the filtering capacity of both the dialyzer and the hemofilter. The control schemes described in conjunction with the following embodiments are intended to regulate the relative filtration rates of the first dialyzer stage 1 and second hemofilter stage 2, denoted "UF1" and "UF2", respectively.

Figure 2:
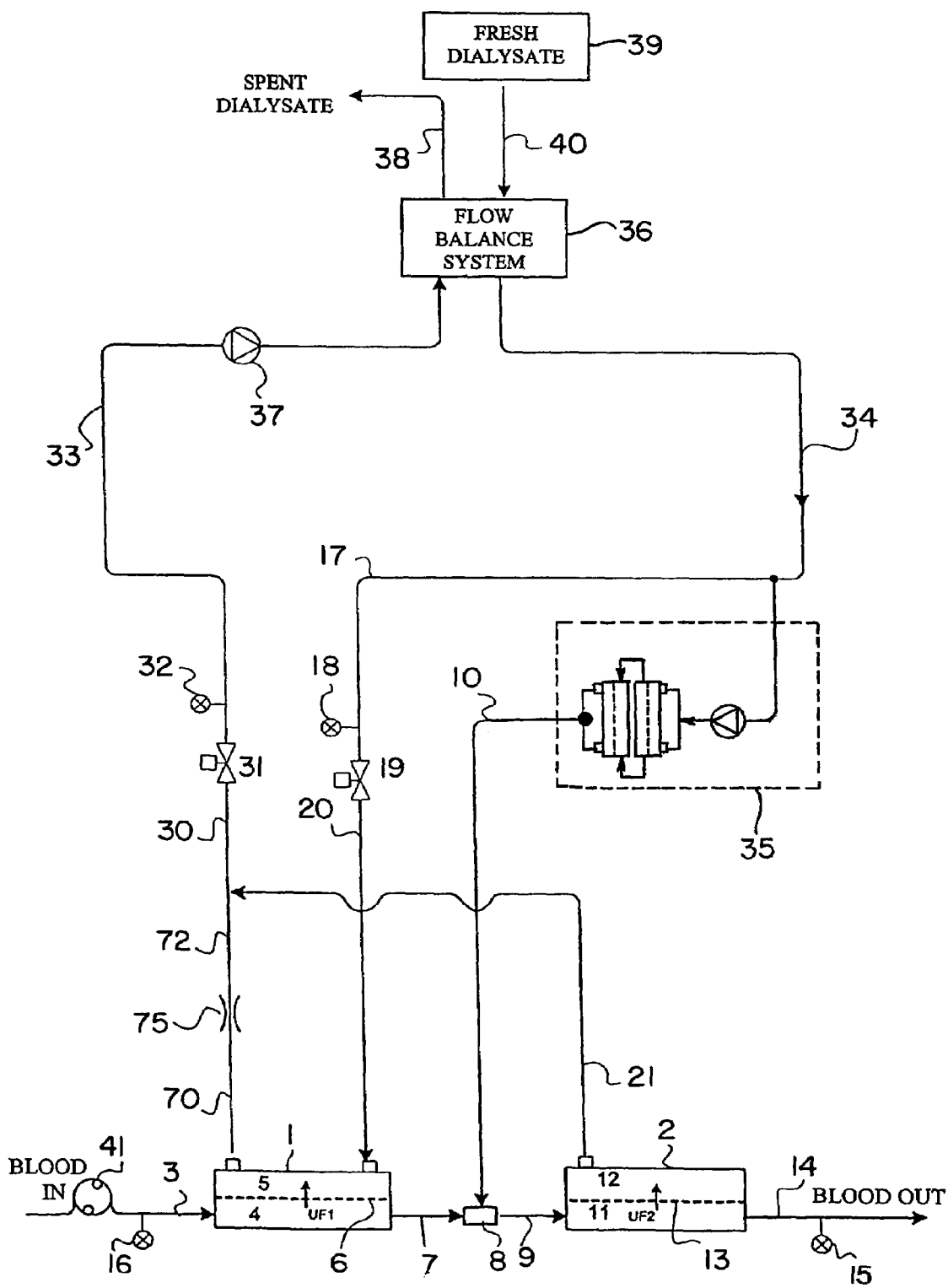
FIG. 2 is a schematic illustration of a two stage hemodiafiltration system in accordance with one embodiment, using a flow restrictor to increase the TMP of the hemofilter stage relative to the dialyzer stage.

Reference is now made to FIG. 2 which schematically illustrates a system generally similar to that of FIG. 1b (wherein identical elements are indicated by identical numerals), with the exception that the system of FIG. 2 includes a flow restrictor 75. The flow restrictor 75 is positioned in the fluid path 70 exiting the dialyzer cartridge 1 prior to combining with the plasma water 21 from the hemofilter cartridge 2. The flow restrictor 75 can be of any type known in the art such as an orifice with a specified diameter and length. The pressure drop across the flow restrictor 75 should be in the range of about 50 to 400 mmHg at dialysate flow rates in the range of about 300 to 1200 ml/min, preferably about 100 to 350 mmHg at dialysate flow rates between 500 to 1000 ml/min. The result of the flow restrictor 75 is to increase the pressure in the dialysate compartment 5 of the dialyzer cartridge 1 while reducing the pressure in the permeate compartment 12 of the hemofilter 2. The effect being to reduce the filtration rate of plasma water (UF1) across the dialyzer membrane 6 while simultaneously increasing the filtration rate of plasma water (UF2) across the hemofilter membrane 13. It should now be obvious to those skilled in the art that using a flow restrictor 75 with a given pressure drop at a given dialysate flow rate it is possible to achieve similar transmembrane pressures in each of the two dialyzer/hemofilter stages at a given blood flow rate and thus achieve a higher total filtration of plasma water (i.e. UF1+UF2).

Figure 3A:
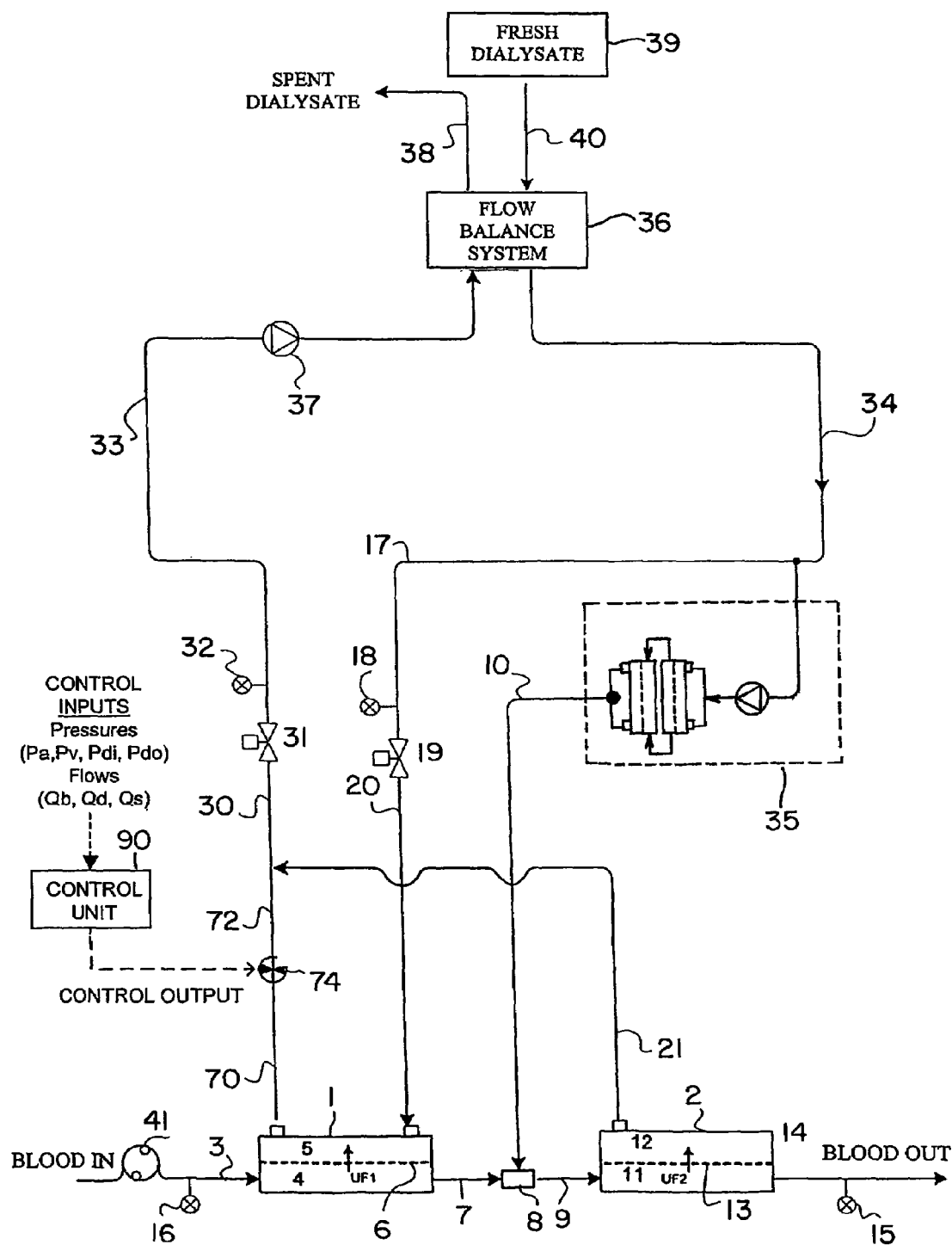
FIG. 3a is a schematic illustration of a two stage hemodiafiltration system in accordance with one embodiment, using a throttling valve controlled by a feedback loop including pressure inputs.

Another embodiment is schematically illustrated in FIG. 3a, wherein a throttling valve 74 is used in place of the flow restrictor 75 as described in the previous embodiment. The throttling valve serves the same function as the fluid restrictor 75 in that it increases the dialysate compartment pressure 5 of the dialyzer cartridge 1 relative to the permeate compartment 12 of the hemofilter cartridge 2. The advantage, however, is that aperture of the throttling valve 74 can be controlled to vary the pressure drop across the valve 74 and thus better regulate the relative filtration occurring in the dialyzer/hemofilter cartridges 1, 2. The throttling valve 74, such as a proportioning valve supplied by South Bend Controls, South Bend, Ind., is such that the aperture opening of the valve 74 is proportional to an applied voltage to the valve. As shown in FIG. 3a, the valve 74 is controlled by closed-loop feedback control using pressure sensor readings, e.g., the inputs indicated in FIG. 3a as Pa, Pv, Pdi, and Pdo, which are received as control inputs by a control unit 90. The control algorithm used by the control unit 90 can set the aperture of the throttling valve 74 so that the TMP of the first and second dialyzers 1, 2 are equalized. An example of such a control scheme may be a scheme which defines a control set point "Delta TMP" as the TMP of first dialyzer minus TMP of second dialyzer. A scheme that sets the control set point Delta TMP to some constant value other than zero may also be used. By defining the TMP of each dialyzer stage as a three point pressure measurement, namely blood in (Pa), blood out (Pv), and dialysate in (Pdi) or out (Pdo), the resulting Delta TMP equation may be simplified to the following:

$$\text{Delta } TMP=0.5*(Pa-Pv)+(Pdo-Pdi)$$

Alternatively, the control algorithm may estimate the total bloodside pressure drop, i.e., (Pa−Pv) in the above equation, based on the blood pump flow rate and substitution pump flow rate. The advantage of this method is that it reduces the number of feedback control inputs being used to two, namely, Pdi and Pdo. For example, the equation for set point Delta TMP may be as follows:

$$\text{Delta } TMP=0.5*(C1*Qb+C2*Qs+C3*[Qs^2]/Qb)+(Pdi-Pdo)$$

wherein Qb is the blood pump rate, Qs is the substitution fluid rate, and C1, C2 and C3 are constants for a given dialyzer combination that may predict blood side pressure drop (Pa−Pv).

Figure 3B:
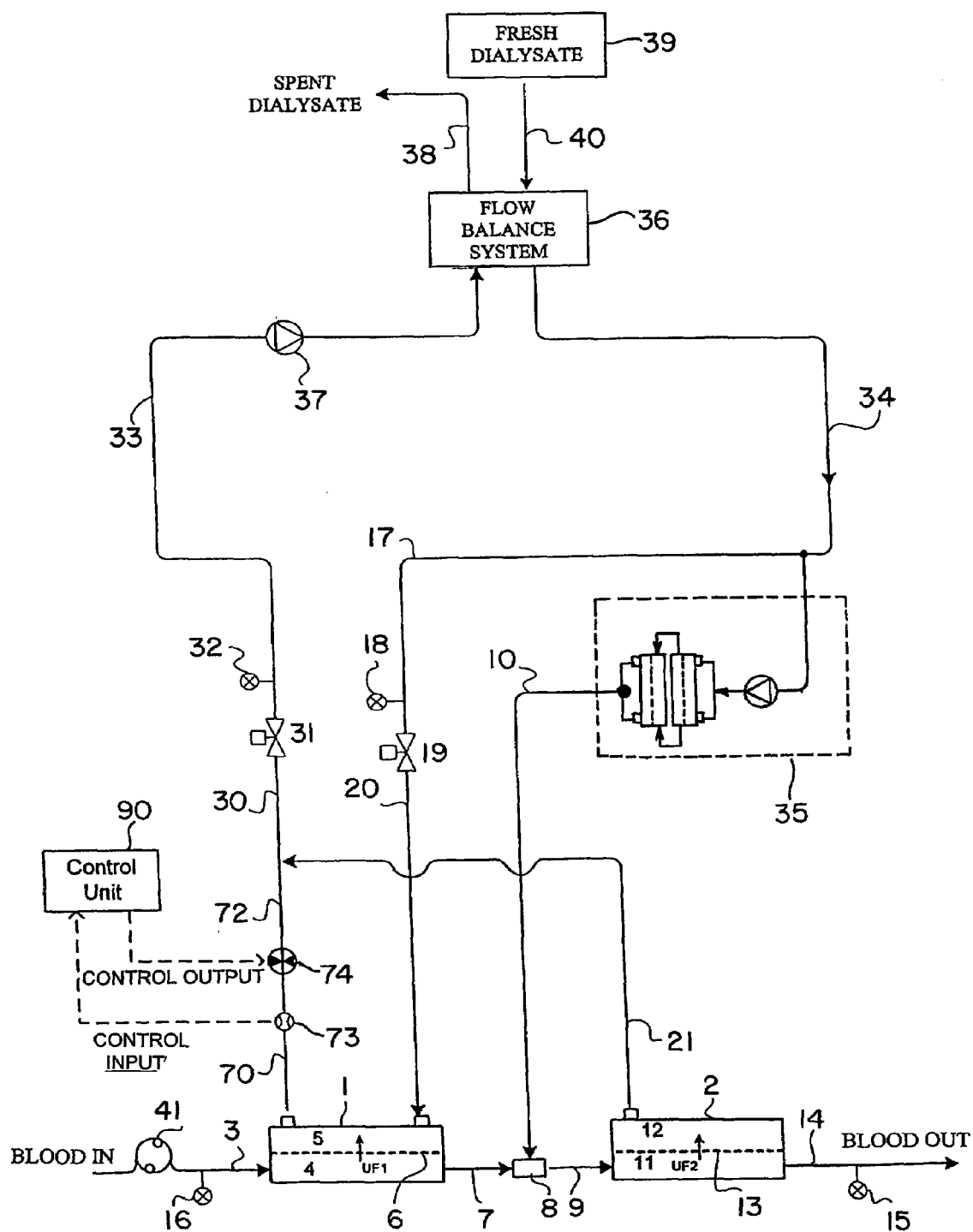
FIG. 3b is a schematic illustration of a two stage hemodiafiltration system in accordance with one embodiment, using a throttling valve controlled by a feedback loop including a flow meter input.

Another embodiment is schematically illustrated in FIG. 3b, wherein a flow meter 73 is used as a feedback control input to the control unit 90 that controls the throttling valve 74. The scheme illustrated in FIG. 3b shows the flow meter 73 located in the dialysate path 70 exiting the first dialyzer 1. The flow meter 73 may be of any type suitable for liquid flow, such as turbine flow meters, fixed volume metering chambers, mass flow meters. For control purposes, the dialysate flow rate, substitution pump rate, and blood pump rate may be used as feed-forward control inputs to control unit 90 to determine the desired set point for the exiting dialysate flow rate. The calculation for determining the set point for the exiting dialysate flow rate (Qd exit) may be performed according to the following formula:

$$Qd \text{ exit}=Qd-Qs*[1+R/(1+R)]$$

wherein Qd is the dialysate flow rate, Qs is the substitution fluid flow rate, and R is a constant defined as the desired ratio of UF1/UF2 (i.e. filtration rate in first dialyzer divided by filtration rate of second hemofilter).

It should be appreciated that although the embodiment of FIG. 3b is described in conjunction with the flow meter 73 in the exiting dialysate stream of dialyzer 1, a similar control scheme based on plasma water flow rate exiting the hemofilter cartridge 2 may be used. Alternatively, a control scheme based on inter-stage blood flow rate exiting the first dialyzer 1 may be readily implemented to control the throttling valve 74. For example, an inter-stage blood flow measuring device (not shown) such as an ultrasonic flow meter available from Transonic Systems, Ithaca, N.Y., USA, may be placed in the blood circuit between the first dialyzer and second hemofilter cartridges 1, 2.

FIG. 3c schematically illustrates yet another embodiment, wherein throttling valve 74 is controlled by a closed-loop feedback control system using a blood hematocrit sensor 85 as a feedback control input to control unit 90. The system illustrated in FIG. 3c includes the in-line blood hematocrit sensor 85 located in the blood path 7 after the blood exits first dialyzer 1. Blood hematocrit sensor 85 may be of a non-invasive type, for example, the "Crit-Line" sensor available from Inline Diagnostics, Kaysville, Utah, USA. Control of the throttling valve 74 is based on a set point for the inter-stage blood hematocrit. The advantage of this scheme is that the system can achieve a higher effective filtration rate in the first dialyzer for situations in which the hematocrit level of the entering blood is below normal, thus maximizing removal efficiency. Additionally, for those situations where the entering blood hematocrit level is above normal, the system does not over-hemoconcentrate the blood in the first dialyzer 1.

Figure 4:
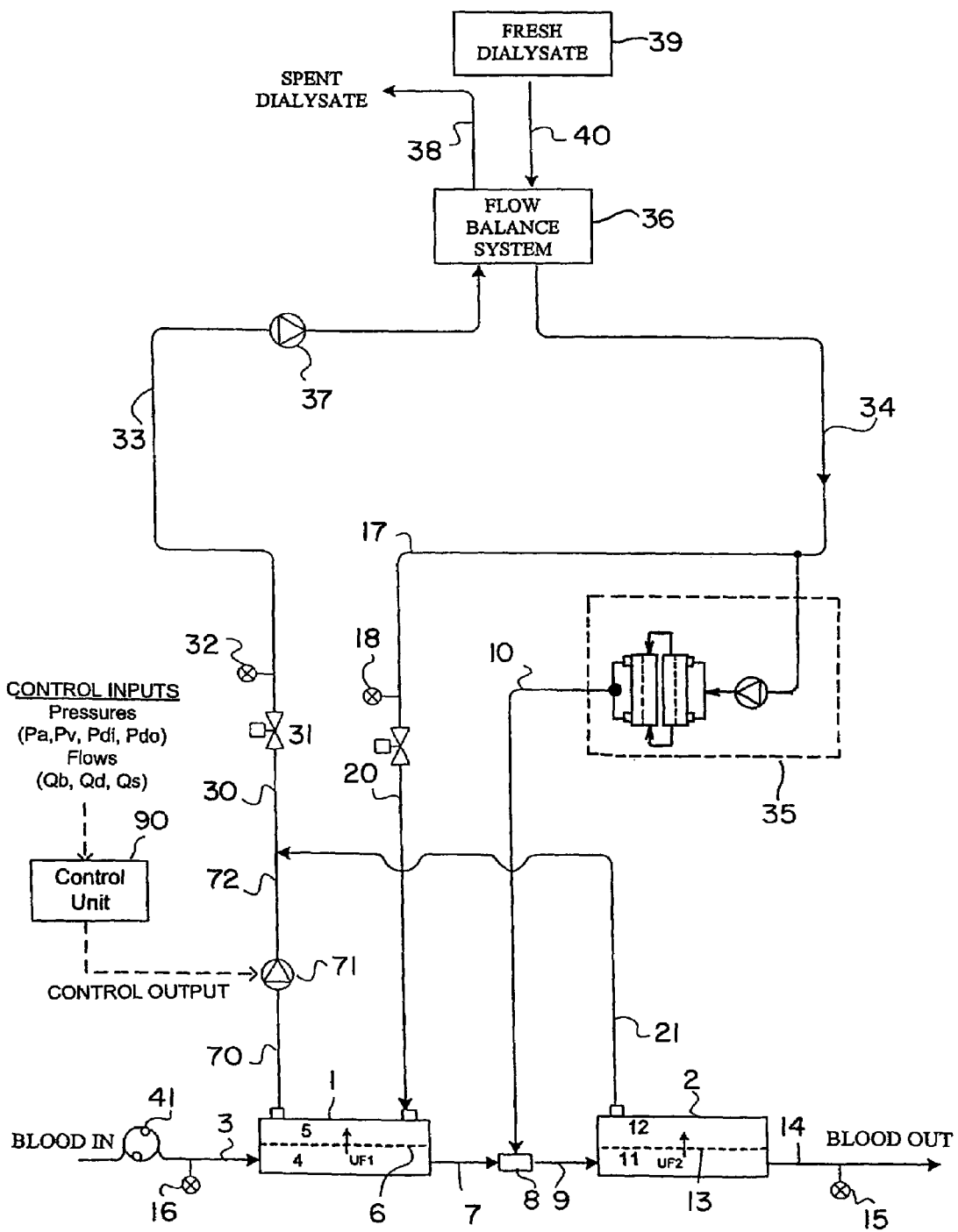
FIG. 4 is a schematic illustration of a two stage hemodiafiltration system in accordance with one embodiment, using a dialysate outlet flow regulating pump controlled by a feedback loop including pressure inputs or a feed-forward loop including dialysate, blood, and substitution flow rate control inputs.

Another embodiment of the invention is schematically illustrated in FIG. 4. In this embodiment, a dialysate outlet flow regulating pump 71 is used in place of the throttling valve 74 (FIG. 3). The flow regulating pump 71 can be either a positive displacement type (e.g. metering pump) or a non-occlusive type (e.g. gear pump) as is known in the art. As shown in FIG. 4, the pump 71 may be controlled by closed-loop feedback control using pressure sensor readings, e.g., the inputs indicated as Pa, Pv, Pdi, and Pdo, which are received as control inputs by a control unit 90. The control algorithm may be similar to that described with reference to FIG. 3a. Additionally or alternatively, by using a positive displacement type pump for the flow regulating pump 71, a closed loop feed-forward control scheme may be used similar to that described with reference to FIG. 3b.

It should be appreciated that although the embodiment of FIG. 4 is described in conjunction with pressure and/or flow rates as control inputs, a control scheme based on inter-stage blood hematocrit exiting the first dialyzer 1 may be readily implemented to control the dialysate outlet flow regulating pump 71.

Figure 5A:
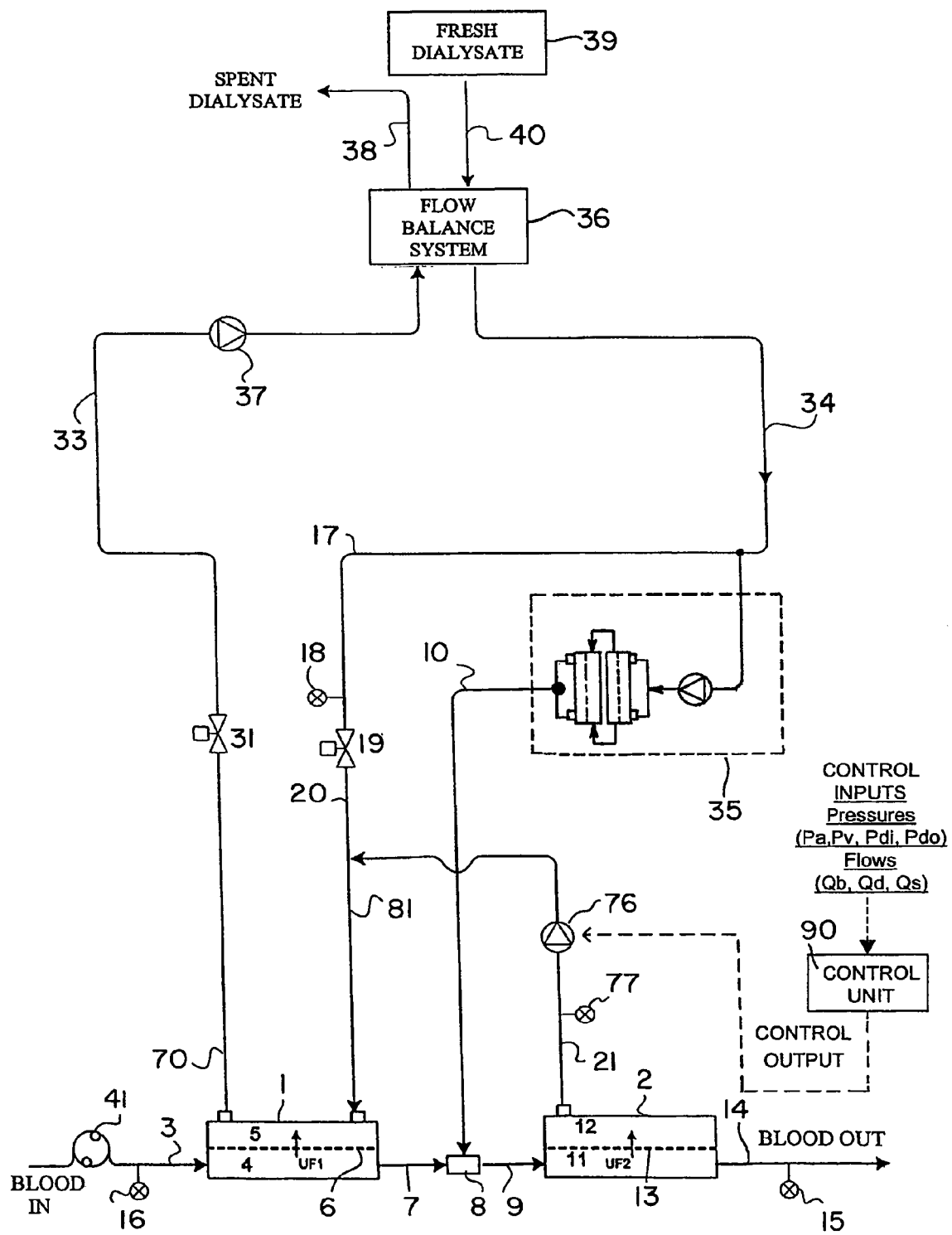
FIG. 5a is a schematic illustration of a two stage hemodiafiltration system in accordance with one embodiment, using a plasma water permeate pump controlled by a feedback loop including pressure inputs or a feed-forward loop including dialysate, blood, and substitution flow rate control inputs.
Figure 5B:
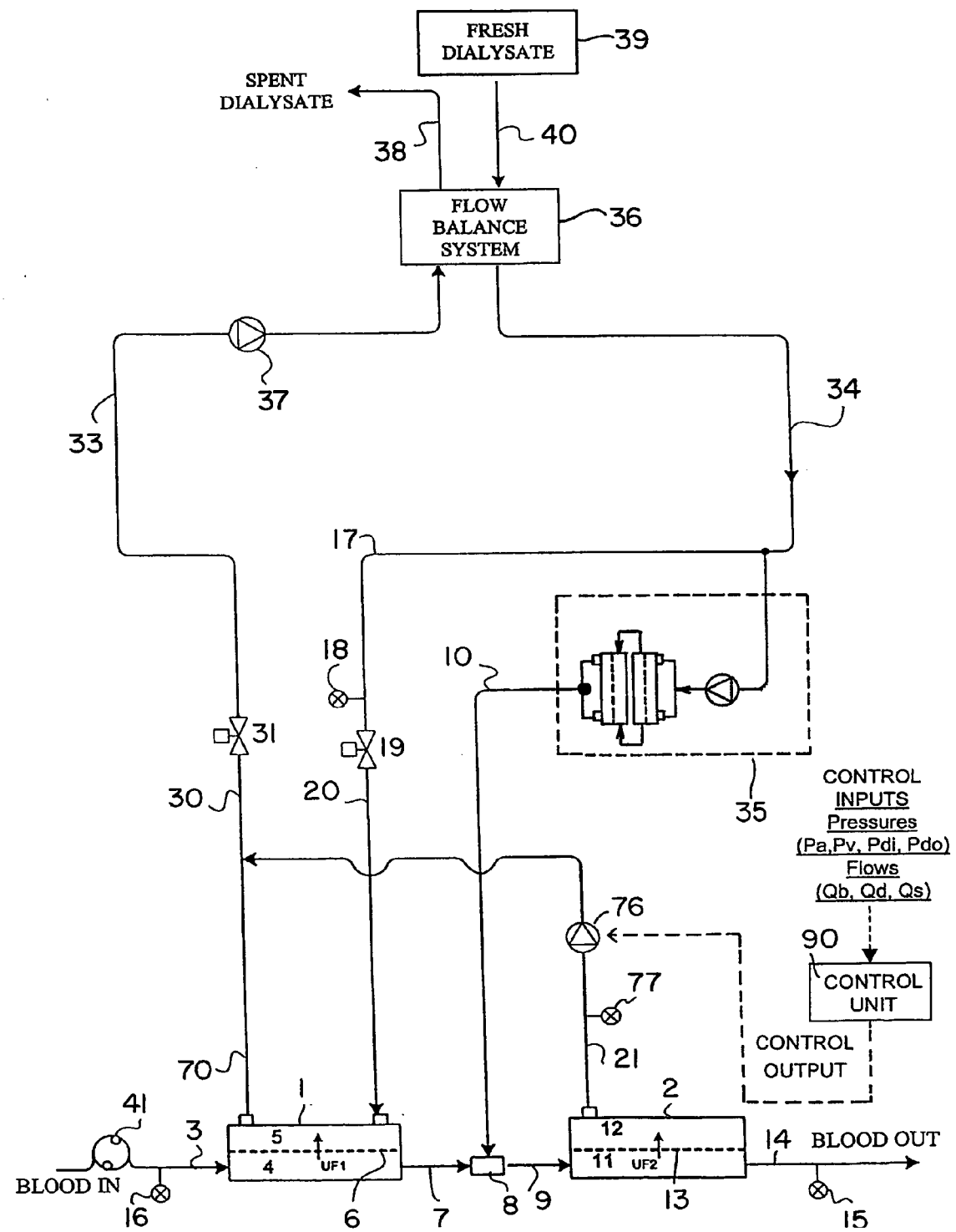
FIG. 5b is a schematic illustration of a two stage hemodiafiltration system in accordance with one embodiment, using a plasma water permeate pump controlled by a feedback loop including pressure inputs or a feed-forward loop including dialysate, blood, and substitution flow rate control inputs, with plasma water from second hemofilter stage bypassing the first dialyzer stage.

FIGS. 5a and 5b describe additional embodiments of the present invention, using a control scheme generally similar to those used in the embodiment of FIG. 4; with the exception that a plasma water permeate pump 76, which may be identical to the flow regulating pump described above with reference to the embodiment of FIG. 4, is used instead of a dialysate outlet flow regulating pump. In the embodiment of FIG. 5a, the plasma water fluid 21 is combined with the fresh dialysate stream 20 to produce a dialysate and plasma water mixture 81 that enters the first dialyzer cartridge 1. In the embodiment of FIG. 5b, the plasma water 21 is combined with the spent dialysate stream 70 to produce a spent dialysate and plasma water mixture 30. The plasma water permeate pump 76 may be a positive displacement type, e.g., a metering pump, or a non-occlusive type pump, e.g. gear pump, as is known in the art. In both embodiments of FIGS. 5a and 5b, the permeate pump 76 is located on the plasma water fluid path 21 exiting the hemofilter 2. The pump 76 may be controlled by closed-loop feedback control using pressure sensor readings, e.g., the inputs indicated as Pa, Pv, Pdi, and Ppo, which are received as control inputs by a control unit 90. The control algorithm may be similar to that described with reference to FIG. 3a, except noting that a plasma water permeate outlet pressure (denoted as "Ppo") of the hemofilter stage is used in place of the dialysate outlet pressure (Pdo) of the dialyzer stage. Additionally or alternatively, by using a positive displacement type pump for the plasma water permeate pump, a closed loop feed-forward control scheme may be used similar to that described per FIG. 3b. In this configuration, the inputs to control unit 90 may include the dialysate flow rate (Qd), substitution fluid pumping rate (Qs) and the blood pumping rate (Qb).

Figure 6A:
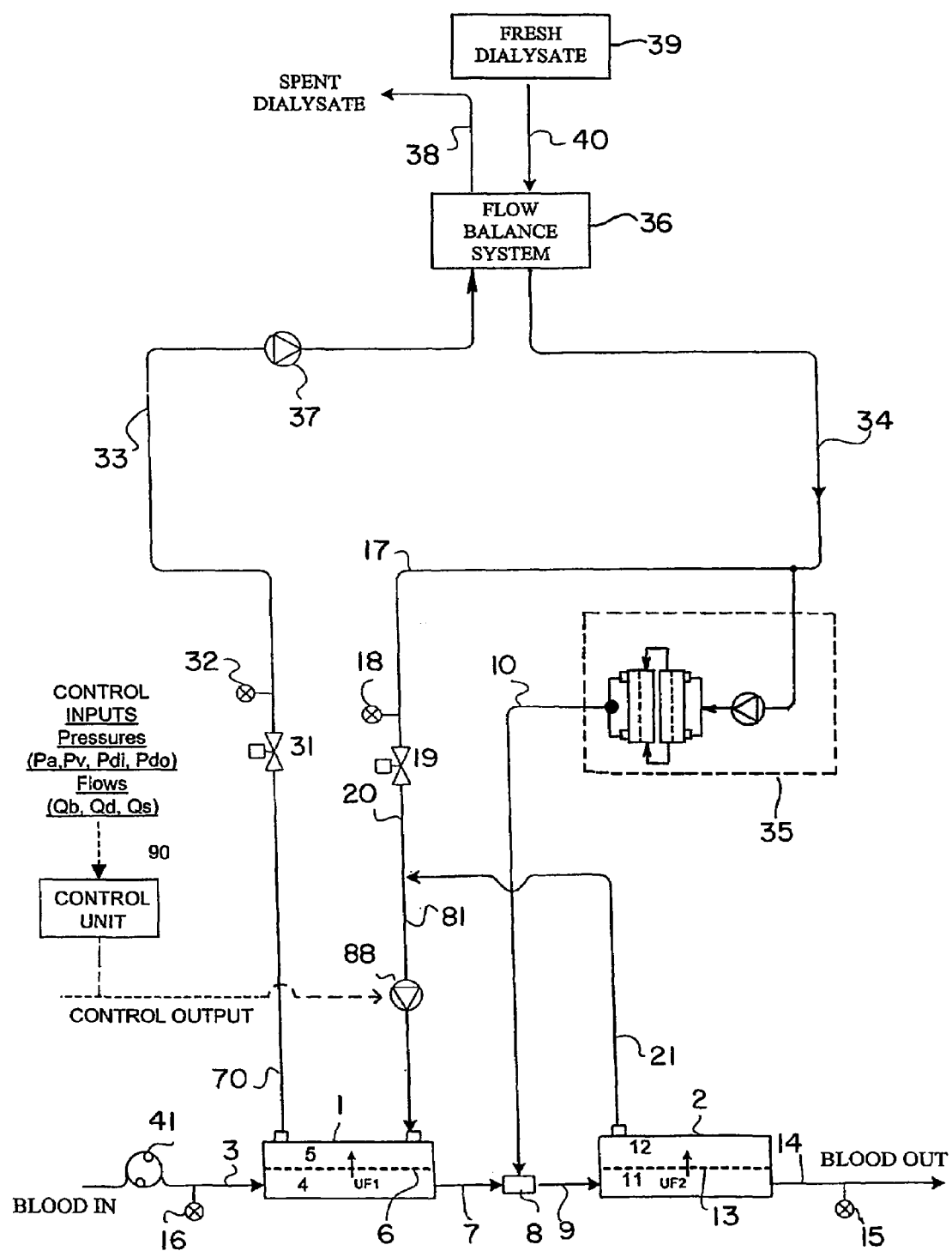
FIG. 6a is a schematic illustration of a two stage hemodiafiltration system in accordance with one embodiment, using a dialysate inlet flow regulating pump controlled by a feedback loop including pressure inputs or a feed-forward loop including dialysate, blood, and substitution flow rate control inputs.
Figure 6B:
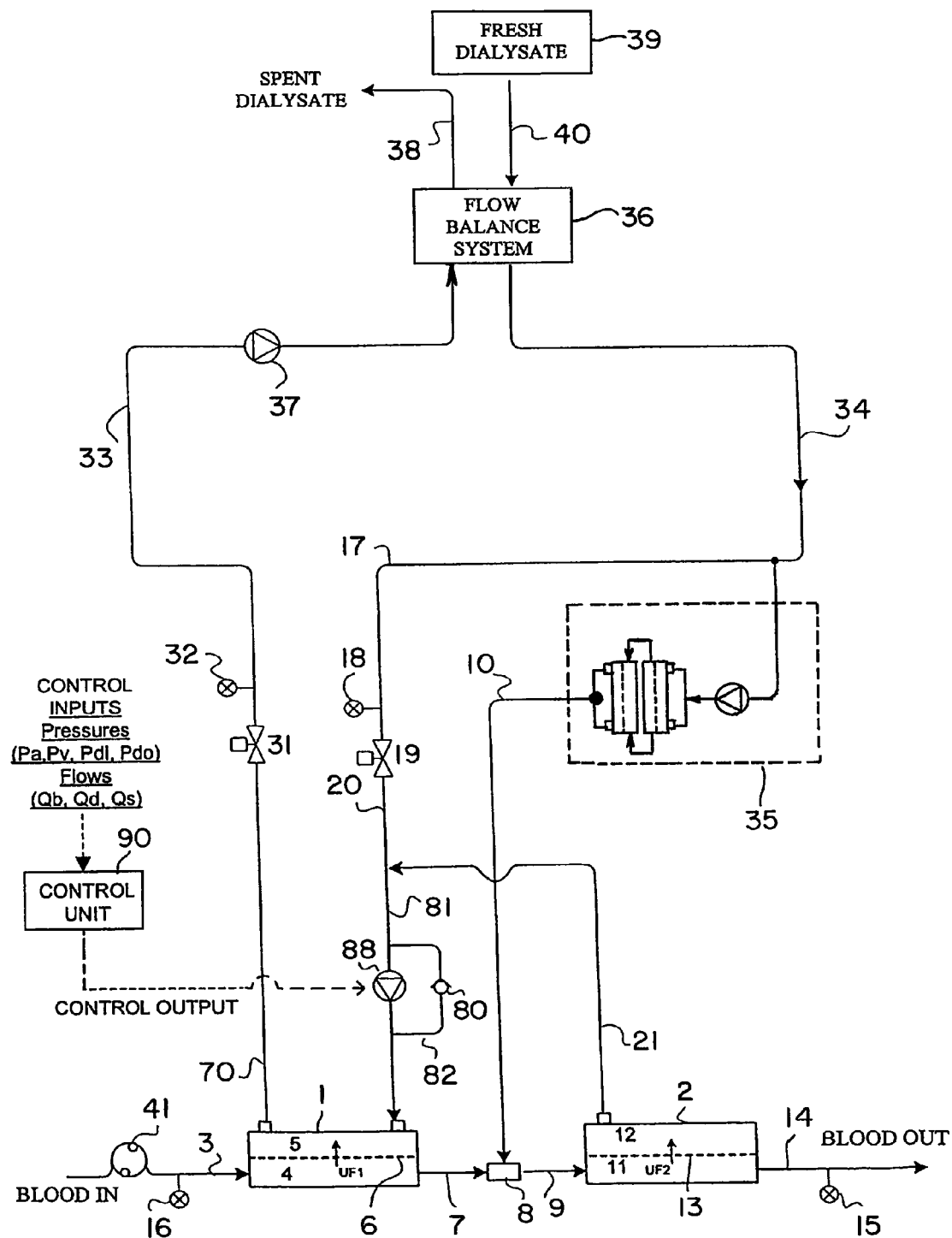
FIG. 6b is a schematic illustration of a two stage hemodiafiltration system in accordance with one embodiment, using a check valve in parallel with a dialysate inlet flow regulating pump, controlled by a feed-forward loop including dialysate and blood flow rate control inputs, eliminating the need for a substitution flow rate control input.

Two additional embodiments of the invention are schematically shown in FIGS. 6a and 6b. Both embodiments use a dialysate flow regulating pump 88 to control the relative filtration rates of the dialyzer/hemofilter stages filtration similar to FIG. 4, however, the dialysate flow regulating pump 88 is placed on the dialysate inlet stream leading to the dialyzer cartridge 1 as opposed to the spent dialysate stream exiting the dialyzer cartridge 1. In each of these embodiments, a fluid mixture 81 comprising fresh dialysate 20 and plasma water 21 is pumped by an inlet flow regulating pump 88. The pump 88 can be either a positive displacement type pump or a non-occluding type pump. In the embodiment of FIG. 6a, control of the inlet flow regulating pump 88 may be similar to that described in the embodiment of FIG. 4. For example, either pressures (Pa, Pv, Pdi, and Pdo) may be used as control inputs in a feed-back control loop scheme or fluid flow rates (Qd, Qb, and Qs) may be used as control inputs in a feed-forward control loop scheme provided a positive displacement type pump is used.

FIG. 6b schematically illustrates yet another embodiment of the invention, wherein the dialysate inlet flow regulating pump 88 is controlled in a closed-loop feed-forward system with the addition of a check valve 80, or a pressure relief valve, which is placed in parallel with flow regulating pump 88. In addition to the advantages of feed-forward control, the configuration of FIG. 6b also has the following advantages. First, the scheme of FIG. 6b does not require use of a positive displacement type pump, which are typically more expensive than non-occluding type pumps. Second, the control algorithm in this scheme may be independent of substitution flow rate (Qs). Third, the control algorithm for this embodiment may establish the maximum filtration rate for the first dialyzer stage UF1. For example, in this configuration, the inputs to the control unit 90 may include dialysate flow rate and blood pumping rate. For control purposes, the dialysate flow rate and blood pumping rate may be used as feed-forward control inputs to the control unit 90 for determining a desired set point for the flow regulating pump rate. For example, in this embodiment, the set point for the inlet flow regulating pump flow rate ("Qd_inlet") may be calculated based on the following formula:

$$Qd\_inlet = Qd - M1 * Qb$$

wherein Qd is the dialysate flow rate, Qb is the blood pump rate, and M1 is a constant based on the maximum percent of the blood flow rate that is filtered in the first dialyzer stage (UF1).

The operation of the system in accordance with the embodiment of FIG. 6b may be as follows. For a given blood flow rate Qb, dialysate flow rate Qd, and a maximum percentage, M1, of the incoming blood flow to be filtered in the first dialyzer, a desired set point may be determined based on the equation above for the inlet flow regulating pump rate. The flow regulating pump may be operated at a specified rate, preferably lower than the dialysate flow rate Qd. For example, at a blood flow rate Qb of 400 ml/min, a dialysate flow Qd of 800 ml/min, and a maximum percentage ultrafiltration (UF) rate M1 of 25% at the first dialyzer, the inlet flow regulating pump rate may be set to 700 ml/min, based on the calculation: 800−0.25*400 ml/min. At zero or low substitution flow rates, the inlet pressure of the flow regulating pump will be higher than the outlet pressure of the pump, despite the pumping action of flow regulating pump. As a result of this pressure difference, a portion of the dialysate/plasma water mixture 81 will flow through check valve 80 via conduit 82, thus bypassing the flow regulating pump. The rate of filtration in the first dialyzer (UF1) is substantially equal to the dialysate flow rate (Qd) minus the sum of the flow regulating pump rate (Qd_inlet) and the flow rate through the check valve (Qcv). As the substitution flow rate (Qs) is increased, the inlet pump pressure upstream of the flow regulating pump 88 decreases relative to the outlet pump pressure. At some point, the inlet pressure to the flow regulating pump becomes lower than the pump outlet pressure. At this point, the flow rate through the check valve (Qcv) is reduced to substantially zero and, thus, the resulting filtration rate of the first dialyzer (UF1) is substantially equal to the dialysate flow rate (Qd) minus the flow regulating pump rate (Qd_inlet). Any further increase in the substitution fluid flow rate decreases the inlet pump pressure which is in fluid communication with the permeate compartment 12 of the hemofilter cartridge 2 causing an increased filtration (UF2). Since the dialysate inlet flow regulating pump rate has not changed, the pressure in dialysate compartment 5 of the first dialyzer remains relatively constant and, thus, does not affect the filtration rate in the first dialyzer (UF1). According to this scheme, the amount of filtration in the first dialyzer stage is limited to a maximum value, "UF1 max", that may be calculated using the following formula:

$$UF1max = M1*Qb$$

Figure 7A:
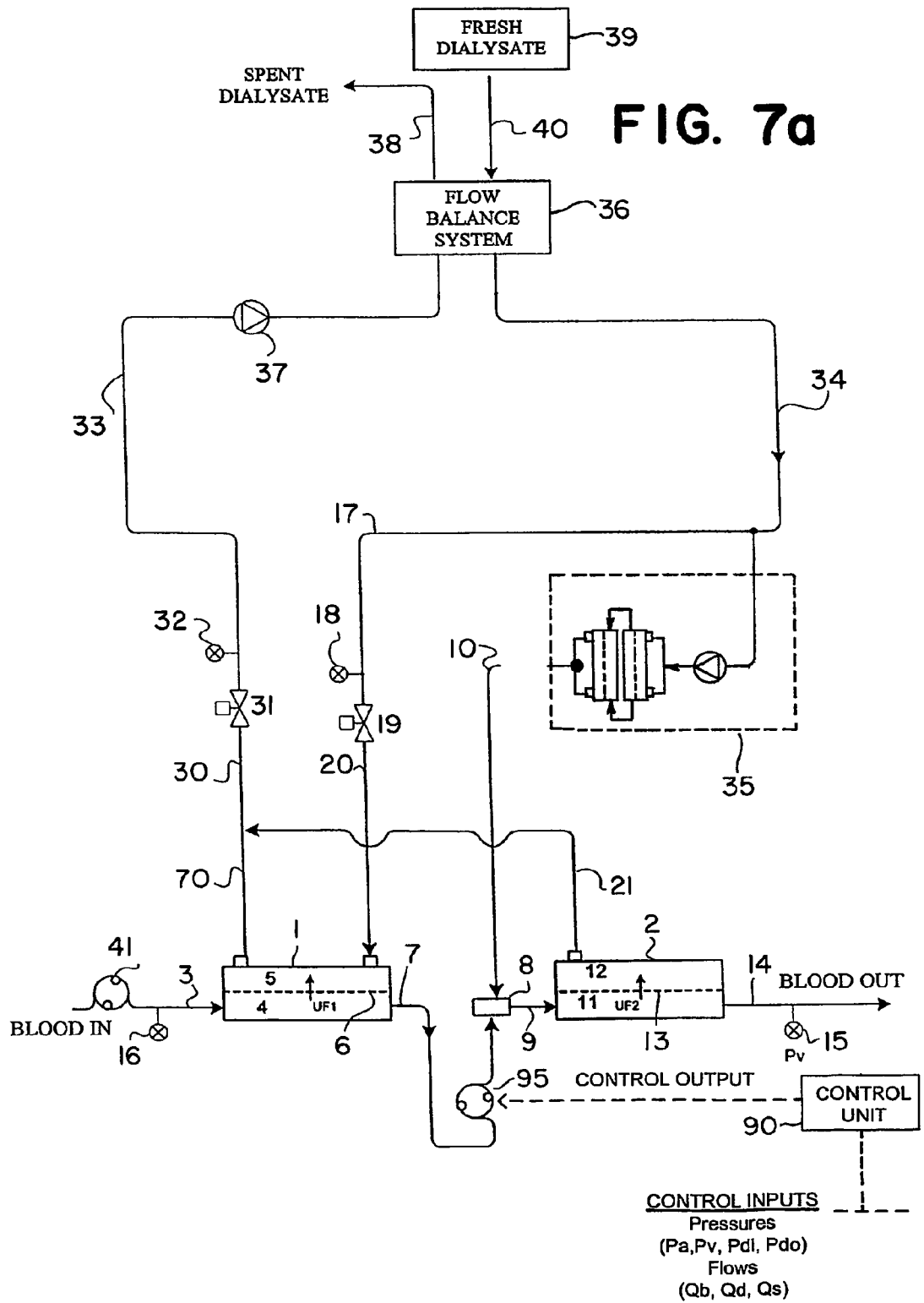
FIG. 7a is a schematic illustration of a two stage hemodiafiltration system in accordance with one embodiment, using an inter-stage blood pump controlled by a feedback loop including pressure inputs or a feed-forward loop including dialysate, blood, and substitution flow rate control inputs.

In the embodiment of FIG. 7a, an inter-stage blood pump 95 is used to control the relative filtration rates of the dialyzer/hemofilter cartridges. Inter-stage blood pump 95 may be a positive displacement type or an occluding type, e.g., a peristaltic type pump, or any other suitable pump type known in the art. As shown in FIG. 7a, blood pump 95 may be placed in the blood circuit between first dialyzer 1 and second hemofilter 2. Blood pump 95 may be placed after the blood exits the first dialyzer 1, as shown in FIG. 7a, or after the blood mixes with the substitution fluid 9 prior to entering the second hemofilter 2. As shown in FIG. 7a, the inter-stage blood pump 95 may be controlled by closed-loop feedback control using pressure sensor readings, e.g., the inputs indicated in FIG. 7a as Pa, Pv, Pdi, and Pdo, which are received as control inputs by a control unit 90. The control algorithm used by controller 90 may set the inter-stage blood pump rate so that the TMP of the dialyzer and hemofilter cartridge stages are equalized in manner similar to that described per FIG. 3a. Alternatively, a feed-forward control scheme based on the incoming blood pump rate (Qb), the dialysate, flow rate (Qd), and the substitution flow rate (Qs) may be readily implemented provided an occlusive type pump is used.

Figure 7B:
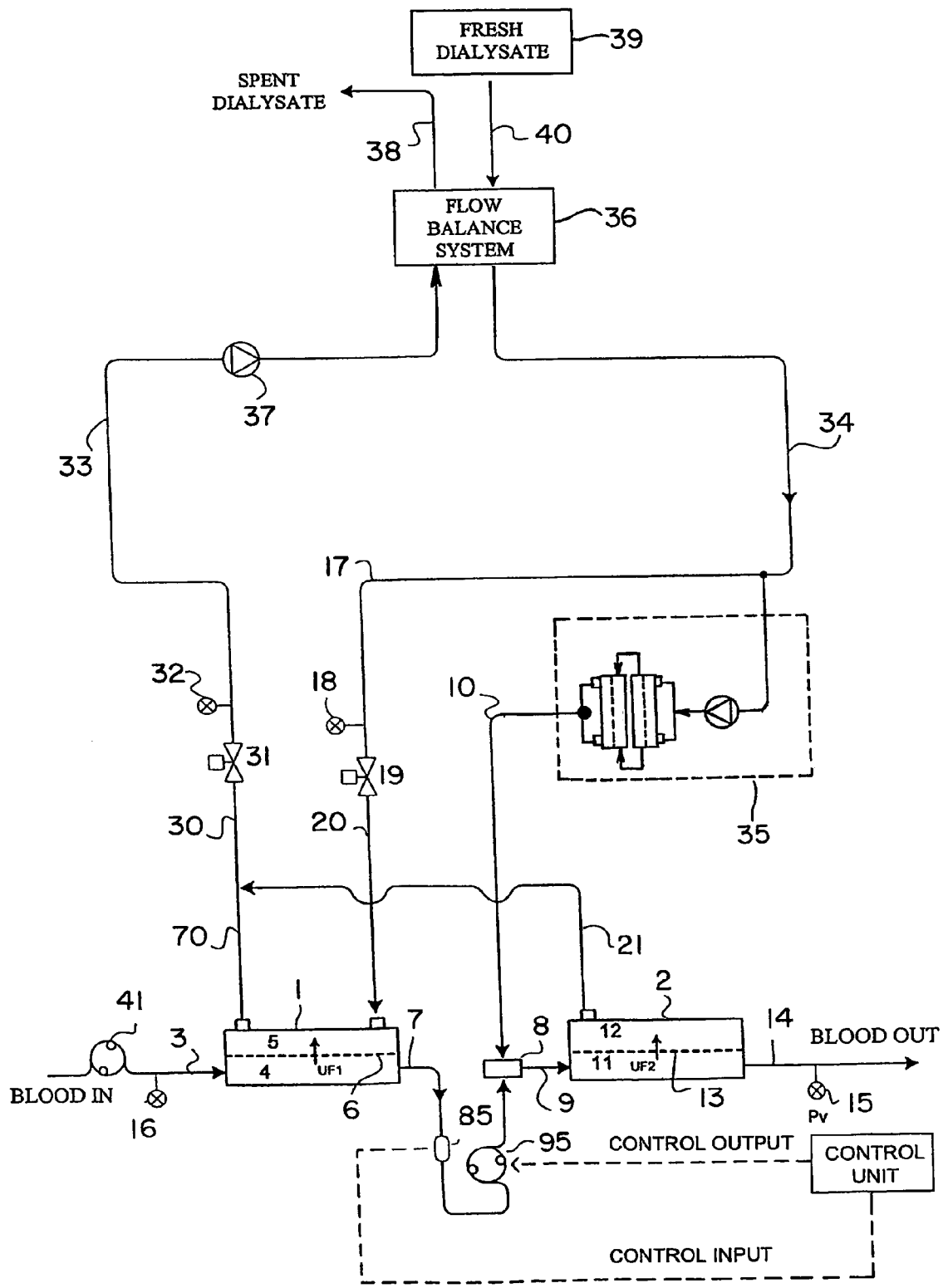
FIG. 7b is a schematic illustration of a two stage hemodiafiltration system in accordance with one embodiment, using an inter-stage blood pump controlled by a feedback loop including an inter-stage blood hematocrit measurement control input.

FIG. 7b schematically illustrates yet another embodiment, wherein inter-stage blood pump 95 is controlled by a closed-loop feedback control system using a blood hematocrit sensor as a feedback control input to control unit 90. The system illustrated in FIG. 7b includes an in-line blood hematocrit sensor 85 located in the blood path 7 after the blood exits first dialyzer 1. Blood hematocrit sensor 85 may be of a non-invasive type, for example, the "Crit-Line" sensor available from Inline Diagnostics, Kaysville, Utah, USA. Control of the inter-stage blood pump is based on a set point for the inter-stage blood hematocrit. The advantage of this scheme is that the system can achieve a higher effective filtration rate in the first dialyzer for situations in which the hematocrit level of the entering blood is below normal, thus maximizing removal efficiency. Additionally, for those situations where the entering blood hematocrit level is above normal, the system does not over-hemoconcentrate the blood in the first dialyzer.

It should be appreciated that although the embodiment of FIG. 7b is described in conjunction with an inter-stage blood pump, a similar control scheme based inter-stage blood hematocrit exiting the first dialyzer may be readily implemented to control a dialysate inlet or outlet flow regulating pump or a plasma water permeate pump instead of the inter-stage blood pump. For example, the dialysate outlet flow regulating pump may be placed after the dialysate exits the first dialyzer 1, the dialysate inlet flow regulating pump may be placed at the dialysate inlet of the first dialyzer 1, or the permeate pump may be placed after plasma water exits the hemofilter 2, such as shown in FIGS. 4, 5(a & b), and 6(a & b) respectively.

Figure 7C:
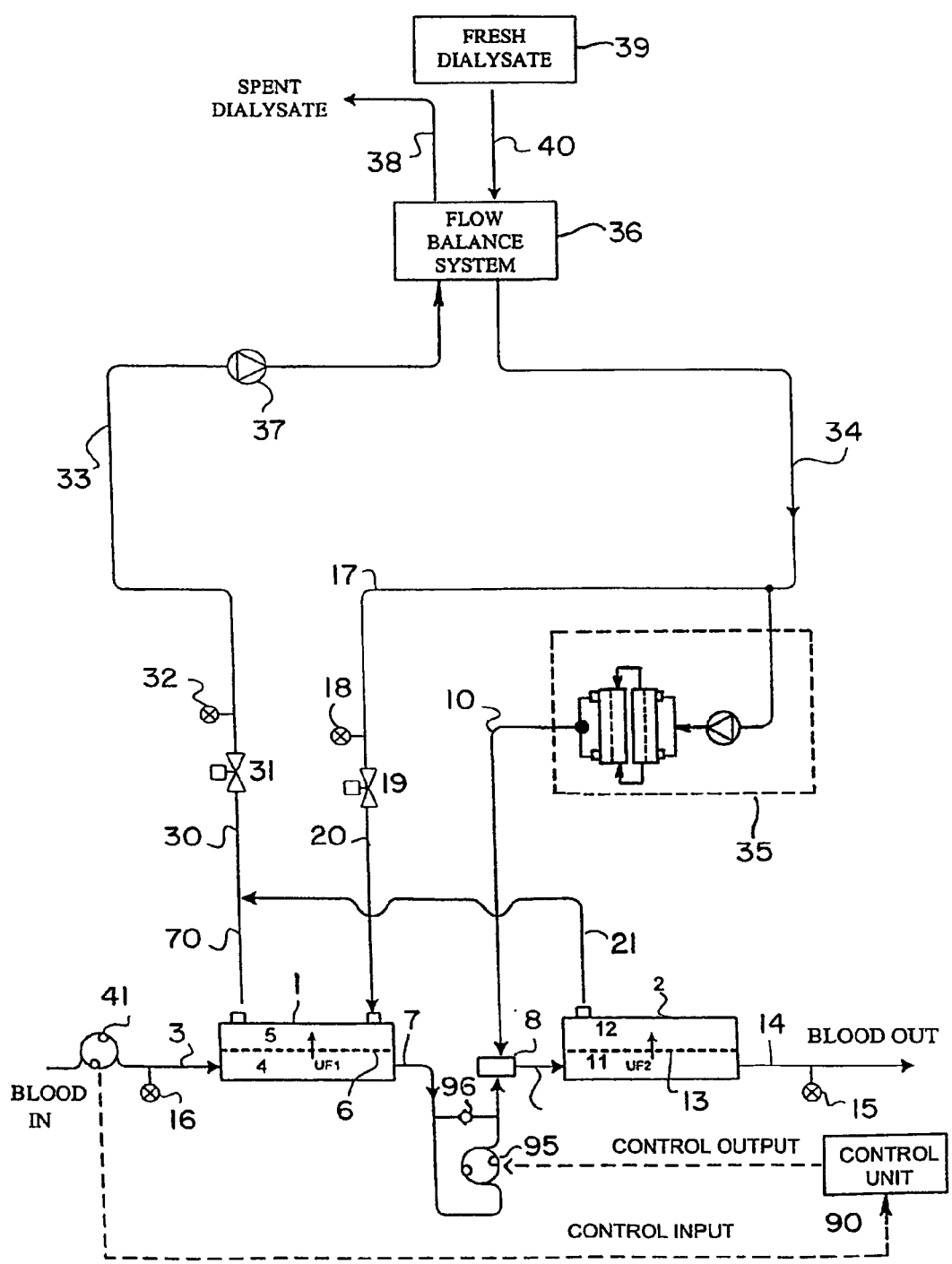
FIG. 7c is a schematic illustration of a two stage hemodiafiltration system in accordance with one embodiment, using a check valve in parallel with an inter-stage blood pump, eliminating the need for substitution flow rate control input.

In the embodiment of FIG. 7c, a check valve 96 (which is preferably of a type suitable for blood contact) is placed in parallel with inter-stage blood pump 95. This has the advantage of allowing blood flow to be shunted past the inter-stage blood pump, thus avoiding pressure build ups that may occur when the two blood pumps, 41 and 95, are running at different rates and the dialysate flow is operated at an "isolated" (or "bypass") mode. In an isolated or bypass mode, the valves 19 and 31 are closed and a bypass valve (not shown) is opened to shunt the flow of fresh dialysate fluid from conduit 17 into conduit 33 leading back to the flow balance system 36.

Both pumps 41 and 95 are preferably occluding type pumps. In this control scheme, the input to inter-stage controller 90 may include the blood pumping rate Qb. For control purposes, the blood pumping rate may be used as a feed-forward input to the inter-stage controller to determine the desired set point for the inter-stage blood flow rate. The set point for the inter-stage blood flow rate ("Qb_interstage") may be calculated, for example, using the following formula:

$$Qb\_interstage = Qb - M1*Qb$$

wherein Qb is the blood pump rate, and M1 is a constant defined as the maximum percent of the blood flow rate that is filtered in the first dialyzer stage (UF1).

The operation of the embodiment of FIG. 7c is described as follows. For a given blood pump rate Qb and maximum percent of the incoming blood flow that is to be filtered in the first dialyzer M1, a set point for the inter-stage blood pump rate is determined based on the above equation. The inter-stage blood pump may be operated at a specified rate, preferably lower than the inlet blood flow rate Qb. For example, at a blood flow rate of 400 ml/min and maximum UF percentage M1 of 25% at the first dialyzer, the inter-stage blood pump rate may be set to about 300 ml/min, based on the calculation: 400−0.25*400 ml/min. At zero or low substitution flow rates, the pressure in the blood compartment 4 of the first dialyzer 1 is higher than the pressure of the blood compartment 11 of second hemofilter 2, despite the pumping action of the inter-stage blood pump 95. As a result of this pressure difference, a portion of the blood flows through check valve 96, thus bypassing inter-stage blood pump 95. At this point, the filtration rate in the first dialyzer (UF1) is substantially equal to the blood flow rate (Qb) minus the sum of the inter-stage blood pump rate (Qb_inter-stage) and the flow rate through the check valve (Qcv). As the substitution flow rate (Qs) is increased, there is an increase in pressure downstream of the inter-stage blood pump due to the influx of substitution fluid into mixing chamber 8. At some point, this pressure becomes higher than the inlet pressure of the inter-stage blood pump. This reduces the flow rate through check valve (Qcv) to substantially zero, and the resulting filtration rate in the first dialyzer (UF1) is substantially equal to the inlet blood flow rate (Qb) minus the inter-stage blood pump rate (Qb_interstage). A subsequent increase in substitution rate causes a pressure increase downstream of the inter-stage blood pump and in the blood compartment of the second hemofilter 2 causing an increased filtration rate (UF2). Since the inter-stage blood pump rate has not changed, the pressure in blood compartment 4 of first dialyzer 1 remains relatively constant and, thus, does not affect the filtration rate in the first dialyzer (UF1). Consequently, the filtration rate in the first dialyzer stage is limited to a maximum value ("UF1 max") that may be calculated using the following formula:

$$UF1max = M1*Qb$$

The present invention thus provides a hemodiafiltration/hemofiltration system and method that provides improved performance compared to traditional systems.

It will be appreciated by persons skilled in the art to which this invention pertains that the invention is not limited to the preferred embodiments and configurations described above and with reference to the accompanying drawings. Rather, the scope of the invention is limited only by the following claims.

What is claimed is:

1. In a blood dialysis system including a source of substitution fluid and a blood dialysis machine, a hemodiafiltration/hemofiltration system comprising: a first dialyzer including: a first semi-permeable membrane partitioning said first dialyzer into: a first blood compartment having a first blood inlet which receives blood to be cleaned and a first blood outlet which discharges partially diafiltered blood; and a first dialysate compartment having a first dialysate inlet and a first dialysate outlet; a mixing chamber for mixing said partially diafiltered blood with substitution fluid from said source to obtain a blood/substitution fluid mixture, a dialysate conduit being connected at one end thereof to the first dialysate outlet for carrying spent dialysate fluid from the first dialysate compartment; a second hemofilter including: a second semi-permeable membrane partitioning said second hemofilter into: a second blood compartment having a second blood inlet which receives said blood/substitution fluid mixture and a second blood outlet which discharges filtered blood; and a second permeate compartment having a second permeate outlet that is connected to one end of a permeate conduit that is attached at its other end to the dialysate conduit for carrying plasma water from the second hemofilter; and a control feature for regulating filtration in at least one of the first dialyzer and the second hemofilter, wherein the control feature is disposed along the dialysate conduit proximate to the first dialysate outlet, with the permeate conduit being attached to the dialysate conduit downstream of the control feature.

2. A system according to claim 1, wherein said control feature comprises: a flow restrictor for selectively raising a first fluid pressure of said first dialysate compartment relative to a second fluid pressure of said second permeate compartment.

3. A system according to claim 2, wherein said flow restrictor is a portion of said dialysate conduit that has a reduced inner diameter that defines an opening of reduced diameter along a predetermined length of said dialysate conduit.

4. A system according to claim 1, wherein the control feature comprises: a fluid throttling valve for selectively raising a first fluid pressure of said first dialysate compartment relative to a second fluid pressure of said second permeate compartment.

5. A system according to claim 4, further comprising: a control unit in communication with said fluid throttling valve for controlling the operation of said throttling valve based on at least one input selected from the group consisting of a dialysate flow rate at said first dialysate outlet; a transmembrane pressure of at least one of said first dialyzer and second hemo filter; and a hematocrit level of the partially diafiltered blood.

6. A system according to claim 4, further comprising: a flow meter disposed along said dialysate conduit between said first dialysate outlet and a location wherein said permeate conduit connects to said dialysate conduit; a control unit in communication with said flow meter and said fluid throttling valve for controlling the operation of said fluid throttling valve in response to input received from said flow meter.

7. A system according to claim 4, further comprising: a blood hematocrit sensor disposed in a blood path between said first dialyzer and said second hemofilter; said blood hematocrit sensor for monitoring the blood hematocrit level; a control unit in communication with said blood hematocrit sensor and said fluid throttling valve for controlling the operation of said fluid throttling valve in response to input received from said blood hematocrit sensor.

8. A system according to claim 1, wherein the control feature comprises: an outlet flow regulating pump being positionable in a number of settings for selectively regulating a first fluid pressure of said first dialysate compartment relative to a second fluid pressure of said second permeate compartment.

9. A system according to claim 8, wherein said pump is positioned in a setting that causes the first fluid pressure to increase relative to the second fluid pressure.

10. A system according to claim 8, further comprising: a control unit in communication with said pump for controlling the operation of said pump and positioning said pump within one of said settings based on an input selected from the group consisting of (1) at least one of a dialysate flow rate, a blood flow rate, and a substitution fluid flow; and (2) a transmembrane pressure of at least one of said first dialyzer and said second hemofilter.

11. In a blood dialysis system including a source of substitution fluid and a blood dialysis machine, a hemodiafiltration/hemofiltration system comprising: a first dialyzer including: a first semi-permeable membrane partitioning said first dialyzer into: a first blood compartment having a first blood inlet which receives blood to be cleaned and a first blood outlet which discharges partially diafiltered blood; and a first dialysate compartment having a first dialysate inlet and a first dialysate outlet; a mixing chamber for mixing said partially diafiltered blood with substitution fluid from said source to obtain a blood/substitution fluid mixture; a second hemofilter including: a second semi-permeable membrane partitioning said second hemofilter into: a second blood compartment having a second blood inlet which receives said blood/substitution fluid mixture and a second blood outlet which discharges filtered blood; and a second permeate compartment having a second permeate outlet; and a control feature for regulating filtration in at least one of said first dialyzer and said second hemofilter, wherein the control feature comprises: a permeate pump disposed along a permeate conduit that is connected at a first end to said second permeate outlet and at a second end to a dialysate conduit that is connected to said first dialysate outlet for carrying dialysate fluid from said first dialysate compartment, said permeate conduit for carrying plasma water from said second hemofilter and being in communication with said dialysate conduit at a location downstream of said permeate pump, said permeate pump for selectively regulating a first fluid pressure of said second permeate compartment relative to a second fluid pressure of said first dialysate compartment.

12. In a blood dialysis system including a source of substitution fluid and a blood dialysis machine, a hemodiafiltration/hemofiltration system comprising: a first dialyzer including: a first semi-permeable membrane partitioning said first dialyzer into: a first blood compartment having a first blood inlet which receives blood to be cleaned and a first blood outlet which discharges blood having a first concentration of toxins; and a first dialysate compartment having a first dialysate inlet and a first dialysate outlet; a mixing chamber for mixing said discharged blood from said first dialyzer with substitution fluid from said first source to obtain a blood/substitution fluid mixture; and a second hemofilter including: a second semi-permeable membrane partitioning said second hemofilter into: a second blood compartment having a second blood inlet which receives said blood/substitution fluid mixture and a second blood outlet which discharges blood having a second concentration of toxins, the first concentration being greater than the second concentration; and a second permeate compartment having a second permeate outlet; and a controller for regulating filtration rates in said first dialyzer and said second hemofilter based upon predetermined input, wherein a dialysate conduit is connected at one end to said first dialysate outlet for carrying spend dialysate fluid from said first dialysate compartment; a permeate conduit connected at one end to said second permeate outlet and being in communication, at an opposite end, with said dialysate conduit; and wherein said permeate conduit carries plasma water that has been filtered across said second semi-permeable membrane to said dialysate conduit, whereby said plasma water bypasses said first dialyzer.

13. A method of hemodiafiltration/hemofiltration comprising the steps of: receiving a blood inflow; diafiltering said blood inflow in a first stage to provide a partially diafiltered blood outflow; mixing said partially diafiltered blood outflow with a substitution fluid to provide a blood/substitution fluid mixture; hemofiltering said blood/substitution fluid mixture in a second stage; and providing a flow control feature in a dialysate conduit that carries spent dialysate fluid from the first stage, connecting a permeate conduit that carries plasma water derived from the second stage to said dialysate conduit at a location downstream of said flow control feature; and wherein the flow control feature permits a hemodiafiltration rate of the first stage and a hemofiltration rate of the second stage to be varied with respect to one another.

14. A method according to claim 13, further comprising the step of: regulating a hemodiafiltration rate of the first stage and a hemofiltration rate of the second stage with a controller based upon predetermined input received by said controller.

15. A method according to claim 13, wherein the flow control feature comprises an operable flow restrictor device and the method further includes the step of: operating said flow restrictor device so that a hemodiafiltration rate of the first stage and a hemofiltration rate of the second stage are varied with respect to one another.

16. A method according to claim 13, wherein the flow control feature comprises a throttling valve and the method further includes the step of operating said throttling valve so that a hemodiafiltration rate of the first stage and a hemofiltration rate of the second stage are varied with respect to one another.

17. A method according to claim 16, wherein the step of operating said throttling valve comprises the steps of: providing a control unit in communication with said throttling valve; disposing a flow meter within said dialysate conduit for detecting a flow rate of said spent dialysate fluid; said flow meter in communication with said control unit; and operating said throttling valve in response to input received by said control unit from said flow meter.

18. A method according to claim 16, wherein the step of operating said throttling valve comprises the steps of: providing a control unit in communication with said throttling valve; disposing a blood hematocrit sensor within a blood conduit for carrying said partially diafiltered blood outflow, said blood hematocrit sensor being located in said blood conduit prior to a location where said substitution fluid is mixed with said partially diafiltered blood outflow; said blood hematocrit sensor in communication with said control unit; and operating said throttling valve in response to input received by said control unit from said blood hematocrit sensor.

19. A method according to claim 13, wherein the flow control feature comprises an outlet flow regulating pump and the method includes the step of operating said outlet flow regulating pump so that a hemodiafiltration rate of the first stage and a hemofiltration rate of the second stage are varied with respect to one another.

20. A method of hemodiafiltration/hemofiltration comprising the steps of: receiving a blood inflow; diafiltering said blood inflow in a first stage to provide a partially diafiltered blood outflow; mixing said partially diafiltered blood outflow with a substitution fluid to provide a blood/substitution fluid mixture; hemofiltering said blood/substitution fluid mixture in a second stage; and disposing a permeate pump in a permeate conduit that carries plasma water derived from the hemofiltering step from said second stage, connecting said permeate conduit at one end to a dialysate conduit that carries spent dialysate derived from said hemodiafiltration step; and operating said permeate pump so that a hemodiafiltration rate of the first stage and a hemo filtration rate of the second stage are varied with respect to one another.

* * * * *